United States Patent
Shachar et al.

(10) Patent No.: US 8,986,214 B2
(45) Date of Patent: Mar. 24, 2015

(54) SYSTEM AND METHOD FOR USING TISSUE CONTACT INFORMATION IN AN AUTOMATED MAPPING OF CARDIAC CHAMBERS EMPLOYING MAGNETICALLY SHAPED FIELDS

(75) Inventors: Yehoshua Shachar, Santa Monica, CA (US); Bruce Marx, Ojai, CA (US); Leslie Farkas, Ojai, CA (US); Eli Gang, Los Angeles, CA (US); Laszlo Farkas, Ojai, CA (US)

(73) Assignee: Magnetecs Inc., Inglewood, CA (US)

( * ) Notice: Subject to any disclaimer, the term of this patent is extended or adjusted under 35 U.S.C. 154(b) by 784 days.

(21) Appl. No.: 12/707,085

(22) Filed: Feb. 17, 2010

(65) Prior Publication Data
US 2010/0305429 A1 Dec. 2, 2010

Related U.S. Application Data

(63) Continuation-in-part of application No. 12/475,370, filed on May 29, 2009, now abandoned.

(51) Int. Cl.
| A61B 5/02 | (2006.01) |
| A61B 5/053 | (2006.01) |
| A61B 5/06 | (2006.01) |
| A61B 5/107 | (2006.01) |
| A61B 5/00 | (2006.01) |
| A61B 5/0402 | (2006.01) |

(52) U.S. Cl.
CPC .............. *A61B 5/0538* (2013.01); *A61B 5/06* (2013.01); *A61B 5/062* (2013.01); *A61B 5/1075* (2013.01); *A61B 5/6851* (2013.01); *A61B 5/6885* (2013.01); *A61B 5/0402* (2013.01); *A61B 5/6852* (2013.01); *A61B 5/6869* (2013.01)
USPC ........................................................ 600/508

(58) Field of Classification Search
None
See application file for complete search history.

(56) References Cited

U.S. PATENT DOCUMENTS

2004/0019447 A1* 1/2004 Shachar ........................ 702/115
2007/0197891 A1* 8/2007 Shachar et al. ............... 600/374

* cited by examiner

*Primary Examiner* — Christopher D Koharski
*Assistant Examiner* — Elizabeth K So
(74) *Attorney, Agent, or Firm* — Marcus C. Dawes; Daniel L. Dawes

(57) ABSTRACT

The invention relates to a method for using tissue contact technology to optimize automated cardiac chamber mapping algorithms to both speed up the mapping process and guarantee the definition of the actual chamber limits. The invention further comprises a method for conveying tissue type information to such automatic mapping algorithms so as to allow them to adapt their point collection density within areas of particular interest. The method is enhanced by the use of a magnetic chamber that employs electromagnetic coils configured as a waveguide that radiate magnetic fields by shaping the necessary flux density axis on and around the catheter distal tip so as to push, pull and rotate the tip on demand and as defined by such automatic mapping algorithms.

16 Claims, 19 Drawing Sheets

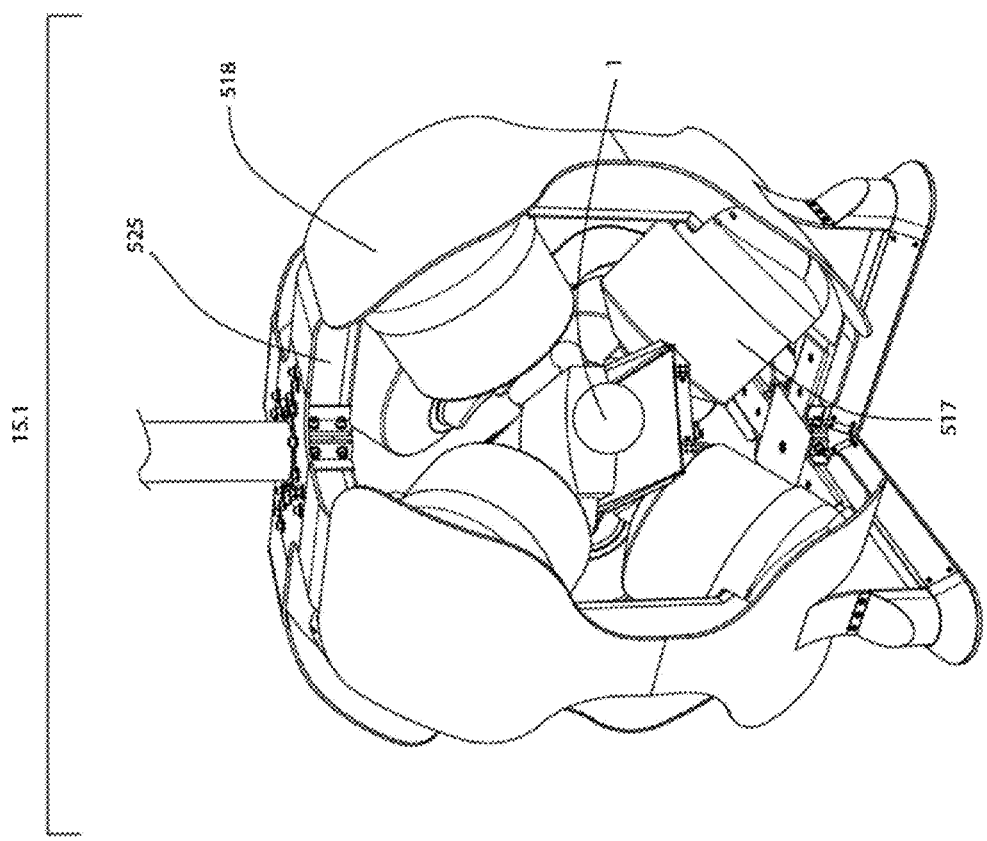

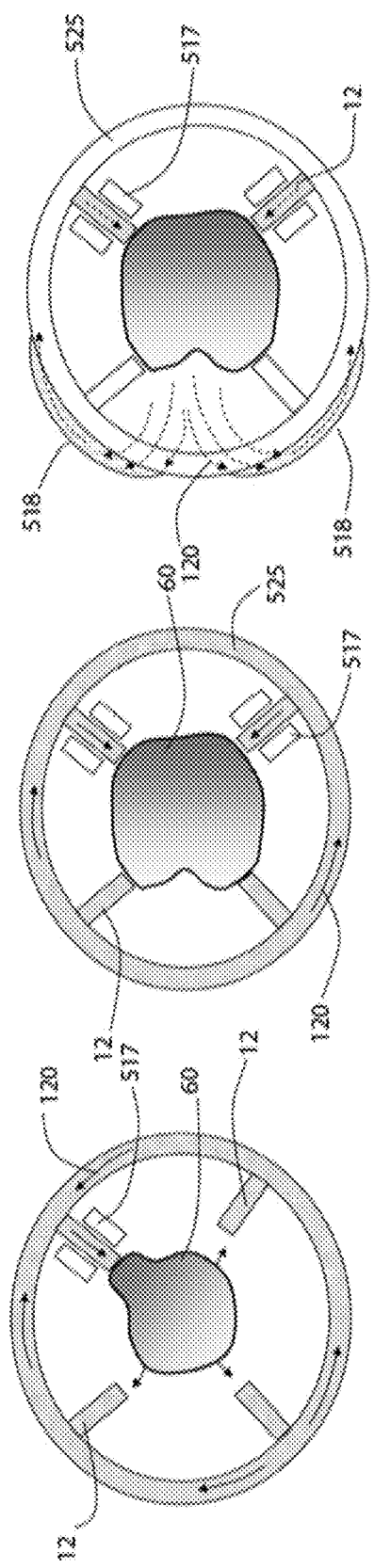

SYSTEM AND METHOD FOR USING TISSUE CONTACT INFORMATION IN AN AUTOMATED MAPPING OF CARDIAC CHAMBERS EMPLOYING MAGNETICALLY SHAPED FIELDS

RELATED APPLICATIONS

The present application is related to U.S. patent application Ser. No. 12/475,370, entitled "Method and Apparatus for Magnetic Waveguide Forming a Shaped Field Employing a Magnetic Aperture for Guiding and Controlling a Medical Device," filed on May 29, 2009, which is incorporated herein by reference and to which priority is claimed pursuant to 35 USC 119.

BACKGROUND OF THE INVENTION

1. Field of the Invention

The invention relates to the field of medical mapping systems, namely systems and methods for guiding, steering and advancing an invasive medical device in a patient for the purpose of defining the physical boundaries and surface properties of a chamber or orifice.

2. Description of the Prior Art

All cardiac electrophysiologic procedures, as currently practiced, involve the use of intracardiac electrode catheters which are placed inside one or more of the four cardiac chambers. Occasionally one or more catheters is also placed in the pericardial space surrounding the heart. The catheters are used for recording intracardiac electrograms, and in many cases the catheters are also used for creating a 3-D representation of the relevant cardiac chamber. Mapping catheters contain an array of electrodes which are used for three purposes: (1) to record local and "far-field" intracardiac electrical activity, (2) to deliver ablative, or curative energy to endocardial surfaces, most commonly in the form of RF energy, and (3) for position location and creation of the chamber geometry. As the catheter is moved about the chamber, the geometric shell of the chamber is defined at the extreme limits of catheter travel, along with the electrical activity on that shell. When the physician determines that there is enough surface detail, the surface is considered to be fully mapped. The physician then uses the display of the endocardial electrogram on the geometric shell to determine specific locations to deliver therapeutic radiofrequency energy. Some electrophysiology laboratories deliver RF energy to specific sites, such as pulmonary vein ostia in the left atrium, without regard to the specific recorded electrogram at those sites. It is also common practiced to integrate or merge the 3-D geometry of the cardiac chamber with a pre-procedure representation of that chamber, usually obtained by a CT or MRI scan.

Prior to many ablation procedures, the relevant cardiac chamber is mapped in order to facilitate the movement of the catheter to precise anatomic regions which are responsible for initiating the arrhythmia. Once a circuit or an arrhythmogenic focus are found, or a specific aberrant tract is located, the catheter is directed the relevant endocardial surface site(s) and an electrode is placed in contact with the endocardial tissue. RF energy is then delivered from the electrode to the tissue to heat and ablate the tissue, thus eliminating the source of the arrhythmia.

Common problems encountered in this procedure are difficulty in precisely locating the aberrant tissue, and complications related to the ablation of the tissue. Locating the area of tissue causing the arrhythmia often involves several hours of electrically "mapping" the inner surface of the heart using a variety of mapping catheters, and once the aberrant tissue is located, it is often difficult to position or maintain the catheter at the desired position in the beating heart so that it continuously maintains contact with the desired tissue.

In the manual method of mapping coronary chambers, the physicians rely on their dexterity to manipulate mapping catheters about the chamber and into the associated vasculature. The density of the mapping data varies due to the time and attention the physician gives each part of the chamber, as well as to the anatomic variability found between individual patients i.e., in some patients certain cardiac anatomic regions are more difficult to reach than in other patients. In addition, the variable amount of force used by the physician in mapping will unevenly distend the chamber walls and create "false cardiac spaces," as well as possibly distort the relationship between the pulmonary vein ostia and the associated left atrial body. The geometric definition of such ostia is critical in determining the locations for the delivery of therapeutic radiofrequency energy.

In both manual and automated mapping procedures, the catheter is swept about the inner surfaces of the cardiac chamber which is undergoing dynamic contractions under the systole/diastole cycle. The locally averaged (motion filtered) position of the catheter at its extreme limits is used to define the boundaries or endocardial surfaces of the relevant cardiac chambers. This type of catheter manipulation does not guarantee that the limit defined by the geometric map completely delineates the true anatomic borders of the cardiac chambers, but rather defines the limit of where the catheter has been.

Prior and related art associated with guiding and controlling an automated mapping and therapeutic procedure are extensive in scope, the discussion outlined by this application is centered on the ability of a novel magnetic chamber enabling such modality of guiding and controlling a mapping and other therapeutic tools in an automated fashion within the heart chambers of a patient.

The prior art as described by U.S. Pat. No. 3,708,772 (Le Franc) describes a highly compact magnetic lens arrangement which economically provides the highest field strength on the axis with the minimum beam half width and a minimum outer field strength of the coil winding which comprises two tubular shielding cylinder means of superconductive material coaxially aligned with the lens axis. The cylinder means each has a first end and a second end, said first ends being spaced from each other to define a unshielded lens gap between, said lens gap having a coil means positioned about the cylinder means to create a magnetic field, a cooling agent adapted to be present about the cylinder which cause a concentration of the magnetic field adjacent the particle beam, and a ferromagnetic ring-shaped pole shoe on each of said first ends of said cylinders for regulating and guiding the magnetic field.

Davis U.S. Pat. No. 4,057,748 teaches a travelling wave tube having a periodic permanent magnetic focusing structure provided with ferromagnetic plates having copper inserts which conduct heat away from the electron beam path and reduce the formation of hot spots.

Purnell U.S. Pat. No. 3,684,914 teaches a travelling wave tube including an envelope, an electron source for projecting an electron beam along a predetermined path in said envelope, a collector spaced from said source for intercepting and collecting electrons in the beam, a helical conductor disposed within said envelope along the path of said beam for supporting and projecting an electromagnetic wave in coupled relationship to the beam for interaction therewith, a periodic permanent magnet focusing assembly having a succession of alternate high thermal conductivity conducting bars and magnetic plates having aligned apertures to define an envelope portion which accommodates the helix support assembly and helix and a plurality of magnet bars disposed between plates to form a succession of longitudinal magnetic fields in coupled relationship with the beam to focus the same as it travels along the envelope portion.

Carson, et al. U.S. Pat. No. 6,078,872 titled "Magnetic lens, method and focus volume imaging MRI" teaches methods for suppressing noise in measurements by correlating functions based on at least two different measurements of a system at two different times. In one embodiment, a measurement operation is performed on at least a portion of a system that has a memory. A property of the system is measured during a first measurement period to produce a first response indicative of a first state of the system. Then the property of the system is measured during a second measurement period to produce a second response indicative of a second state of the system. The second measurement is performed after evolution duration subsequent to the first measurement period when the system still retains a degree of memory of an aspect of the first state. Next, a first function of the first response is combined with a second function of the second response to form a second-order correlation function. Information of the system is then extracted from the second-order correlation function.

In general, the prior art is centered on the ability of microscopic resonance imaging, spectrometry, and general resonance imaging to form a coherent magnetic field for use in MR imaging. Maxwell's equations place restrictions on the properties of magnetostatic fields in free space. It is impossible for the magnitudes of the components of the magnetic field vector $B_X$, $B_Y$, or $B_Z$ to have a local minimum or maximum in free space. Additionally, the magnetic field magnitude, $|B|$, cannot have a local maximum, but it can have local minimum in free space. Localized minimums have been generated with current carrying structures and used in the fields of plasma confinement, neutral particle trapping, and levitation. Others have also proposed magnetic resonance imaging techniques that were based on different physical principles for creating what the papers termed as an imaging focus point, and relied on the magnetic field gradients produced by the three-dimensional current carrying wires. See, Damadian, et al., "Field Focusing Nuclear Magnetic Resonance (FONAR): Visualization of a Tumor in a Live Animal," Science 194, 1430 (1976); Hinshaw, "Image Formation by Nuclear Magnetic Resonance: The Sensitive Point Method," J. Appl. Phys. 47, 3709 (1976). The current carrying structures limit practical extensions of the technique. All the above noted patents and journal publications are the results of the ability of microscopic resonance imaging, spectrometry, and general resonance imaging to form a coherent magnetic field for use in MR imaging. The novel and application of the waveguide and its magnetic aperture depart from the prior art due to the embodiments which this application teaches.

What is needed is a new waveguide and magnetic aperture that enables the creation of an electroanatomic map by using an apparatus that automatically performs the task of mapping of an anatomical site.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole. Additional objects and advantages of the current invention will become apparent to one of ordinary skill in the art upon reading the specification.

Some embodiments of the method of this invention provides for automatically mapping an anatomical surface of a subject's heart with the help of a remote navigation system. One example of such a system is the Catheter Guidance, Control & Imaging Apparatus (CGCI), described by U.S. Pat. Nos. 1,521,555 and ZL03821597.7, and "System and Method for Radar-Assisted Catheter Guidance and Control", U.S. Pat. No. 7,280,863, and "Apparatus and Method for Shaped Magnetic Field Control for Catheter, Guidance, Control, and Imaging" U.S. Pat. No. 1,895,930 and HK1111875.

The invention described herein solves these and other problems by enhancing the automation of the coronary chamber mapping process with a method using constant magnetic force and position control to seek continuous tissue contact in a distinct set of locations. This method incorporates a tissue contact monitoring algorithm into the coronary chamber mapping algorithms. This contact monitoring determines both intermittent and continuous contact with the moving tissue surface. This allows the automated mapping algorithm to rapidly map out the actual chamber limits in a consistent and repeatable manner. This geometric map may then be used under automatic guidance with a CGCI system to locate ablation catheters and to deliver therapeutic radiofrequency energy.

In one embodiment of the invention, the catheter is controlled by a magnetic catheter guidance, control and imaging system (CGCI) that uses tissue contact information, such as that disclosed in patent application Ser. No. 12/323,231 entitled "System and Method for a Catheter Impedance Seeking Device", Shachar et. al., Nov. 25, 2008 which is incorporated herein by reference in its entirety.

In one embodiment of the invention, the tissue contact information is recorded over several heartbeat cycles and the recording is analyzed to determine the continuity of tissue contact.

In another embodiment of the invention, the catheter is advanced to the tissue surface until continuous contact is made throughout the systole/diastole cycle.

In yet another embodiment of the invention, the catheter is retracted from continuous tissue contact until only partial contact is made, and then the catheter is repositioned and advanced to a new location of continuous tissue contact.

In one embodiment of the invention, a set of distinct directions or coordinate points is sequentially specified to the catheter guidance control and imaging system so as to provide an optimal tissue contact mapping pattern.

In another embodiment of the invention, the differences in tissue contact impedances are used to differentiate between types of tissue within the coronary chamber.

In yet another embodiment of the invention, the differences in the tissue type are used to vary the mapping density of an automated mapping algorithm.

In one embodiment of the invention, the system differentiates between contact with the coronary chamber wall and the associated vasculature for the purpose of locating and defining the vascular ostia.

In one embodiment, the physical catheter tip (the distal end of the catheter) includes a permanent magnet that responds to the magnetic field generated externally by the waveguide. The external magnetic field pulls, pushes, turns, and holds the tip in the desired position. One of ordinary skill in the art will recognize that the permanent magnet can be replaced or augmented by an electromagnet.

One embodiment provides for a waveguide and its regulating apparatus that is more intuitive and simpler to use, that displays the catheter tip location in three dimensions, that applies force at the catheter tip to pull, push, turn, or hold the tip as desired, and that is configured to producing a vibratory or pulsating motion of the tip with adjustable frequency and amplitude.

An additional embodiment provides tactile feedback at the operator control to indicate an obstruction encountered by the tip.

One embodiment of the waveguide and its regulator comprises a user input device called a "virtual tip" (VT). The virtual tip includes a physical assembly, similar to a joystick, which is manipulated by the surgeon/operator and delivers tactile feedback to the surgeon in the appropriate axis or axes if the actual tip encounters an obstacle. The virtual tip includes a joystick type device that allows the surgeon to guide actual surgical tool such as catheter tip through the patient's body. When the actual catheter tip encounters an obstacle, the virtual tip provides tactile force feedback to the surgeon to indicate the presence of the obstacle.

In another embodiment, the waveguide multi-coil cluster is configured to generate a magnetic field gradient for exerting an orthogonal force on the tip (side-ways movement), with little or no rotating torque on the tip. This is useful for example to align the catheter's tip at narrow forks of artery passages.

In one embodiment, the waveguide multi-coil cluster is configured to generate a mixed magnetic field to push/pull and/or bend/rotate the distal end of the catheter tip, so as to guide the tip while it is moving in a curved space.

In one embodiment, the waveguide multi-coil cluster is configured to move the location of the magnetic field in 3D space relative to a desired area. This magnetic shape control function provides efficient field shaping to produce magnetic fields required for example in surgical tool manipulations in the operating region.

In one embodiment, the waveguide symmetry (eight coil clusters) configuration, which enable a regulator to compute the desired field(s) under the doctrine of linear transformation of all matrices in the magnetic chamber so as to enable closure of all vector field operations (addition, subtraction, superposition etc.) without the need for tailoring the waveguide-regulator linearity and thus preserving symmetry within the effective space.

In one embodiment, the waveguide regulator as described and disclosed by Foreign Patent Numbers 1895930 and HK1111875 entitled "Apparatus and Method for Shaped Magnetic Field Control for Catheter, Guidance, Control & Imaging," is used to provided for a means to allow the electromagnet poles faces to form a shaped magnetic field based on a position and orientation of the catheter's travel path between the desired point (DP) and actual point (AP). This method further optimizes the necessary power requirements needed to push, pull, and rotate the surgical tool tip with a minimum of power by employing "lensing" modes of the field. The invention is further improved by the use of the magnetic aperture disclosed above by enabling the waveguide apparatus to form a shaped magnetic field (Flux Density Axis relative to the catheter tip) relative to the minimal geometrical path between AP to DP.

In one embodiment, the waveguide is fitted with a sensory apparatus for real time detection of position and orientation so as to provide command inputs to a servo system that controls the tool-tip location from AP to DP. The waveguide further generates a command which results in the shaping of the magnetic field geometry based on magneto-optical principles as shall be clear when reviewing the figures and the accompanying descriptions detailed herein.

In one embodiment, the waveguide's servo system has a correction input that compensates for the dynamic position of a body part, or organ, such as the heart, thereby offsetting the response such that the actual tip moves substantially in unison with the dynamic position (e.g., with the beating heart). Further, synchronization of dynamic position of a surgical tool with the appropriate magnetic field force and direction is accomplished by the response of the waveguide regulator and its resulting field's intensity and field's geometry.

In another embodiment, the operator can make further adjustments to the virtual catheter tip (VT) position and repeat the sequence of operating steps. In one embodiment, the feedback from the servo system and control apparatus (the regulator) deploys command logic (AI routine) when the actual catheter tip encounters an obstacle or resistance in its path. The command logic is further used to control stepper motors which are physically coupled to the virtual catheter tip.

In one embodiment, a mathematical model for predicting the magnetic field geometry (Shaped) versus magnetic field strength is established relative to the catheter tip axis of magnetization and is used by the waveguide regulator to predict and command the movements of a surgical tool from its actual position (AP) to its desired position (DP).

In one embodiment, the waveguide magnetic chamber comprises a regulator coupled to a magnetically fitted tool which forms a system operated by the steps of:

i) the operator adjusts the physical position of the virtual tip (VT), ii) a change in the virtual tip position is encoded and provided along with data from a position detection system, iii) the regulator generates a series of servo system commands that are sent to a servo system control circuitry, iv) the servo system control apparatus operates the servo mechanisms to adjust the condition of one or more electromagnet from the cluster by varying the power relative to distance and/or angle of the electromagnet clusters vis-a-vie the tool's permanent magnet position, further energizing the electromagnets so as to control the magnetic (catheter) tip within the patient's body, v) the new position of the actual catheter tip is then sensed by the position detection system thereby allowing, for example, a synchronization of the catheter position on an image produced by fluoroscopy, and/or other imaging modality such as ICE, MRI, CT or PET scan, vi) providing feedback to the servo system control apparatus and to the operator interface vii) updating the displayed image of the catheter tip position in relation to the patient's internal body structures, viii) once the catheter tip is positioned at the DP site, the tissue contact information in the automatic mapping function is set by the operator and the catheter is enabled to commence and perform the ablating procedure.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visual-

BRIEF DESCRIPTION OF THE DRAWINGS

FIG. 7C is a perspective view of the CGCI waveguide system shown in FIG. 7B with a patient inserted between the electromagnetic coils.

FIG. 13A is a schematic representation of the geometry of a magnetic field produced by the waveguide assembly.

FIG. 13B is a schematic representation of the geometry of an alternative magnetic field produced by the waveguide assembly.

FIG. 13C is a schematic representation of the geometry of an alternative magnetic fields produced by the waveguide assembly and its magnetic apertures.

Figure 1:
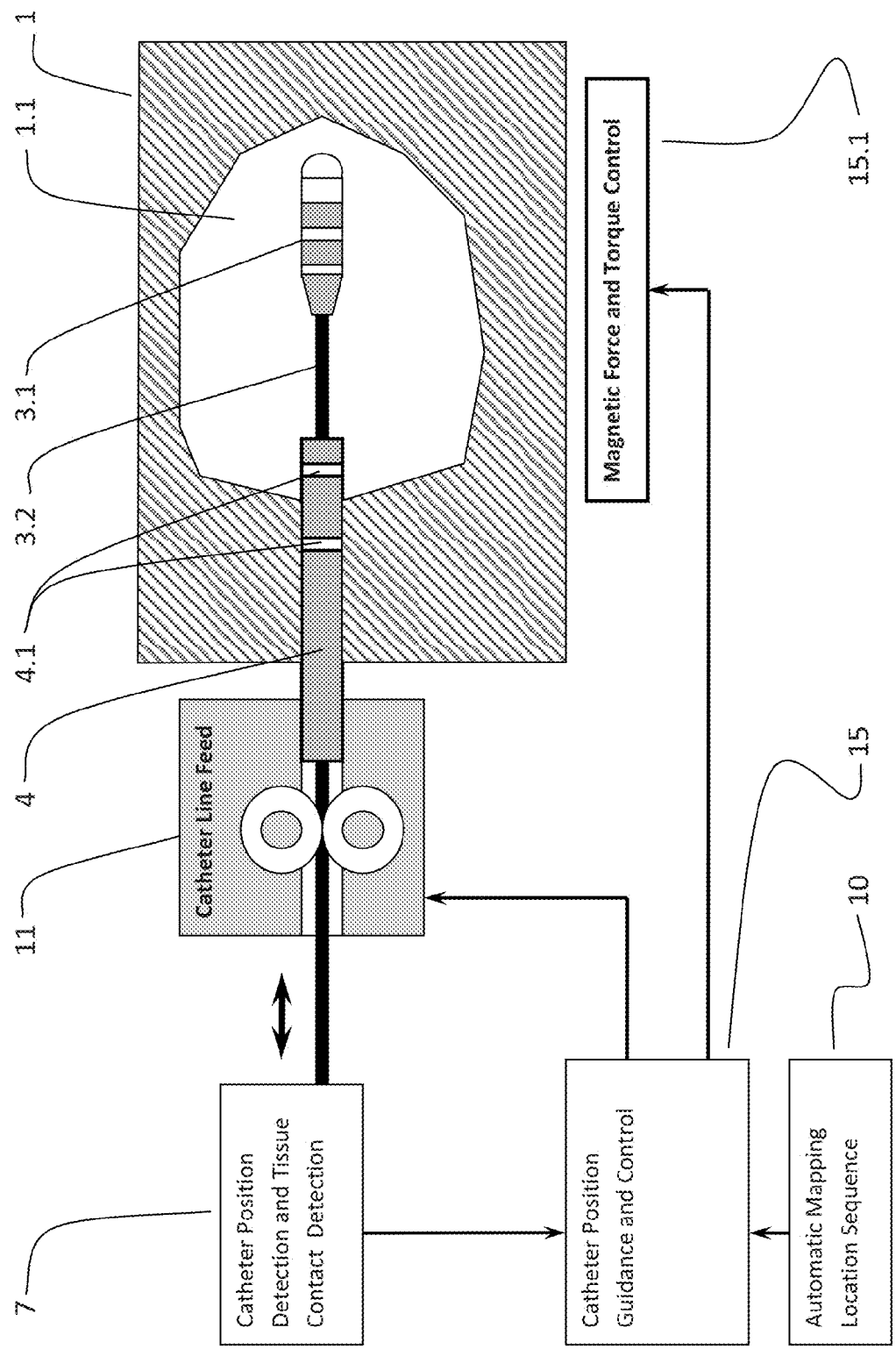
FIG. 1 is block diagram of a catheter guidance control and imaging system (CGCI) using tissue contact information.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DEFINITIONS

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the materials and methodologies which are reported in the publications which might be used in connection with the invention. Nothing herein is to be construed as an admission that the invention is not entitled to antedate such disclosure by virtue of prior invention Ablation—as used herein refers to the use of a catheter to apply radiofrequency electrical energy to a specific location within the heart to necrotize (kill) tissue and block neural conduction pathways as to eliminate electrical signals that are the cause of cardiac arrhythmias.

Ablation Catheter—as used herein refers to a catheter whose tip electrode is wired to deliver radiofrequency energy and also contains a thermocouple for monitoring the tip temperature during the ablation.

Actual Position (AP)—as used herein refers to the six degree of freedom position and orientation of the catheter tip. The catheter tip position is measured at the center of the distal electrode.

Automatic Guidance—as used herein refers to methods of automatically advancing, steering and pushing a catheter toward a desired position.

Catheter—as used herein refers to a minimally invasive medical tool used for diagnostic and therapeutic medical procedures. Catheters have a wide variety of shapes, sizes and capabilities, but all are a combination of a long shaft and a functional end effector.

Desired Position (DP)—as used herein refers to the desired or target six degree of freedom position and orientation of the catheter tip, or the three degree of freedom desired location for a catheter tip with an implied optimized catheter orientation which is based on the orientation of the tissue. Three degree of freedom desired positions are typically used, and the catheter guidance system adjusts the orientation of the catheter for maintaining optimal contact with a moving surface.

Distal—as used herein refers to at the most distant end, or the end of the catheter furthest within the patient.

Electrode—as used herein refers to a conductive ring on a catheter which is wired through the catheter line to the position detection and heart electrogram sensing hardware.

Electrogram—as used herein refers to a time vs. amplitude plot of the electrical potential as measured at a specific point on, or in the body. Electrograms for each electrode pair are displayed on the mapping system and on a separate ECG system.

Electrophysiology—as used herein refesr to the diagnosis and treatment of anomalies in the heart neuro-electrical system.

Geometric Location—as used herein refers to a specific Cartesian point on the geometric map which represents the average position of the tissue location that passes through that point.

Insert Ring—as used herein refers to a ferrous material with permeability of one order magnitude lower than the poleface.

Mapping—as used herein refers to the process of sweeping a catheter about a coronary chamber to define the average location of the walls and the electrical activity of the nerves within those walls throughout the heartbeat cycle.

Poleface—as used herein refers to an aperture comprising of ferrous material formed with a specific geometry and a high permeability (μ>1000) value. In this application the use of a magnetic aperture forming the lense is designated by reference as $4.3x_y$ while the "x" is a designator of the permeability μ (x=μ) value, while "y" is (y=geometry).

Sheath (Introducer)—as used herein refers to a tube which is inserted through a vein and into the heart. Catheters, wires and fluids are introduced into the heart chamber through this tube.

Six Degree of Freedom—as used herein refers to a coordinate set that describes both the position of an object and its orientation in space.

Spiral Catheter—as used herein refers to a type of mapping catheter, typically with twenty electrodes arranged along its coiled end. Manual controls are provided to adjust the amount of coil to make it larger or smaller, as well as to bend the assembly back and forth during the manual mapping process.

Tissue Contact—as used herein refers to where the tip of the catheter maintains continuous contact with the surface of the heart chamber wall throughout the heartbeat cycle.

Shaped Magnetic Field—as used herein refers to a system of forming a shape magnetic field geometry (Lobe), which operates under the principles noted by the invention and as described below.

Lens—as used herein refers to an apparatus used in a CGCI system which generates a DC magnetic field, with magnetic geometry on demand by the use of combination of different material permeability's. The "lens" comprises a ferromagnetic core having an anisotropy axis permanently magnetized in a direction perpendicular to the insert ring, the insert ring being disposed in the magnetic field such that the anisotropy axis is opposite the magnetization direction of the DC magnetic field, the pole face encircled by the ring having cut-outs shaped and dimensioned to create a localized minimum of the magnitude of the magnetic field vector of the combined magnetic field in a focus volume away from the aperture.

Magnetic Aperture—as used herein refers to the optical behavior of ferrous materials having negative permeability at or near permeability resonance which can yield large field amplifications and can refract the flux lines through negative angles. This enhancement is guided analytically by the Biot-Savart law and the inclusion of mirror image currents. (See: *An Open Magnet Utilizing Ferro-Refraction Current Magnification*, by, Yuly Pulyer and Mirko I. Hrovat, Journal of Magnetic Resonance 154, 298-302 (2002)).

Virtual Tip or (VT)—as used herein refers to a physical assembly, similar to a joystick, which is manipulated by the surgeon/operator and delivers tactile feedback to the surgeon in the appropriate axis or axes if the actual tip encounters an obstacle.

CGCI—as used herein refers to a system for guiding and controlling a medical device within a body of a patient: composing of a set of electromagnets formed with a specific geometry and act as a waveguide to deliver electromagnetic radiation acting on a permanent magnet further delivering energy in a manner so as to push, pull, and rotate a surgical tool(s) fitted with such. The CGCI chamber is a highly compact magnetic aperture assembly which economically provides the highest field strength on the axis with the minimum DC field and minimum outer field strength of the coil winding. The assembly is fitted with a parabolic shielding antenna and eight electromagnets coaxially aligned with the lens axis, said chamber means each having a first end and a second end, said first ends being spaced from each other to define a unshielded lens gap there between, said lens gap having a coil means positioned about the chamber to create a magnetic field, a cooling agent adapted to be present about the chamber which cause a concentration of the magnetic field adjacent to a permanent magnet tool, and a ferromagnetic ring-shaped pole face on each of said first ends of said coil for regulating and guiding the magnetic field.

Detailed Description of the Preferred Embodiments

The present invention is a method for guiding an interventional device in a magnetic environment comprising the steps of providing a magnetic navigation system, placing a catheter with an electrode array within a magnetic environment generated by a plurality electromagnets, using a sensor interface to receive signals from the catheter and, in response, generating a processed signal, using a processing and control unit to receive the processed signal and to calculate a position of the electrode array, and using the calculated position of the catheter to guide movement of the catheter within the waveguide environment.

FIG. 1 is block diagram of a catheter guidance control and imaging system that uses tissue contact information. An introducing sheath 4 is inserted into a patient 1 until the distal end is within a cavity or chamber 1.1 to be mapped. The introducing sheath 4 comprises a plurality of position detection electrodes 4.1 which are used to determine both the position of the distal end and the exit direction of the sheath 4. A catheter 3.2 is inserted through the sheath 4 until its distal tip 3.1 is within the chamber 1.1. The proximal section of the catheter line 3.2 is inserted between the rollers of a catheter line feed device 11 that is used by a catheter position guidance and control unit or CGCI regulator 15 to adjust the length of the catheter 3.2 within the chamber 1.1. The distal end of the catheter 3.2 is connected to a catheter position detection and tissue contact detection system 7, such as a St. Jude Medical's EnSite NavX system. This catheter position detection and tissue contact detection system 7 provides the catheter position guidance and control unit 15 with real-time position feedback for the introducer sheath 4 and for the catheter tip 3.1. It also gives tissue impedance readings for a plurality of catheter tip electrodes (not shown). In this embodiment, the catheter position guidance and control unit 15 controls the position of a magnetized catheter tip 3.1 through the use of a plurality of magnetic coils that provide both magnetic torque and force gradients, such as those described in U.S. patent application Ser. No. 11/697,690, "Method and Apparatus for Controlling Catheter Positioning and Orientation", Shachar et. al., Mar. 7, 2008 which is incorporated herein by reference in its entirety. An automated mapping location sequence 10 is a set of targeting locations or directions that are sequentially fed into the catheter position guidance and control unit 15. The pattern and density of the automated mapping location sequence 10 may be a user selectable fixed pattern, or the mapping density may be automatically adjusted based on the current tissue type as acquired from tissue impedance measurements.

Figure 1B:
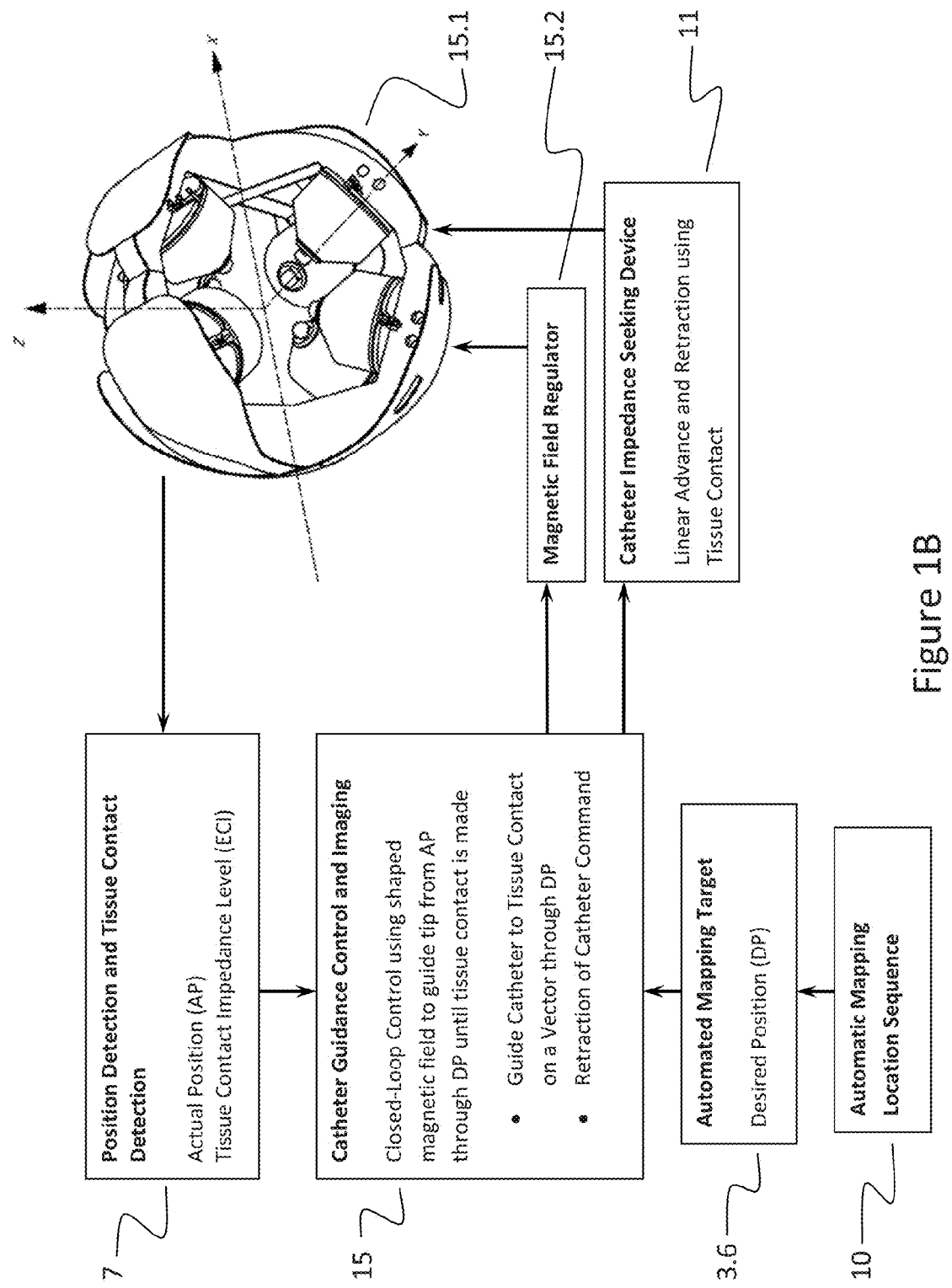
FIG. 1B is a block diagram of the catheter guidance control and imaging system (CGCI) used to guide the catheter into tissue contact.
Figure 9:
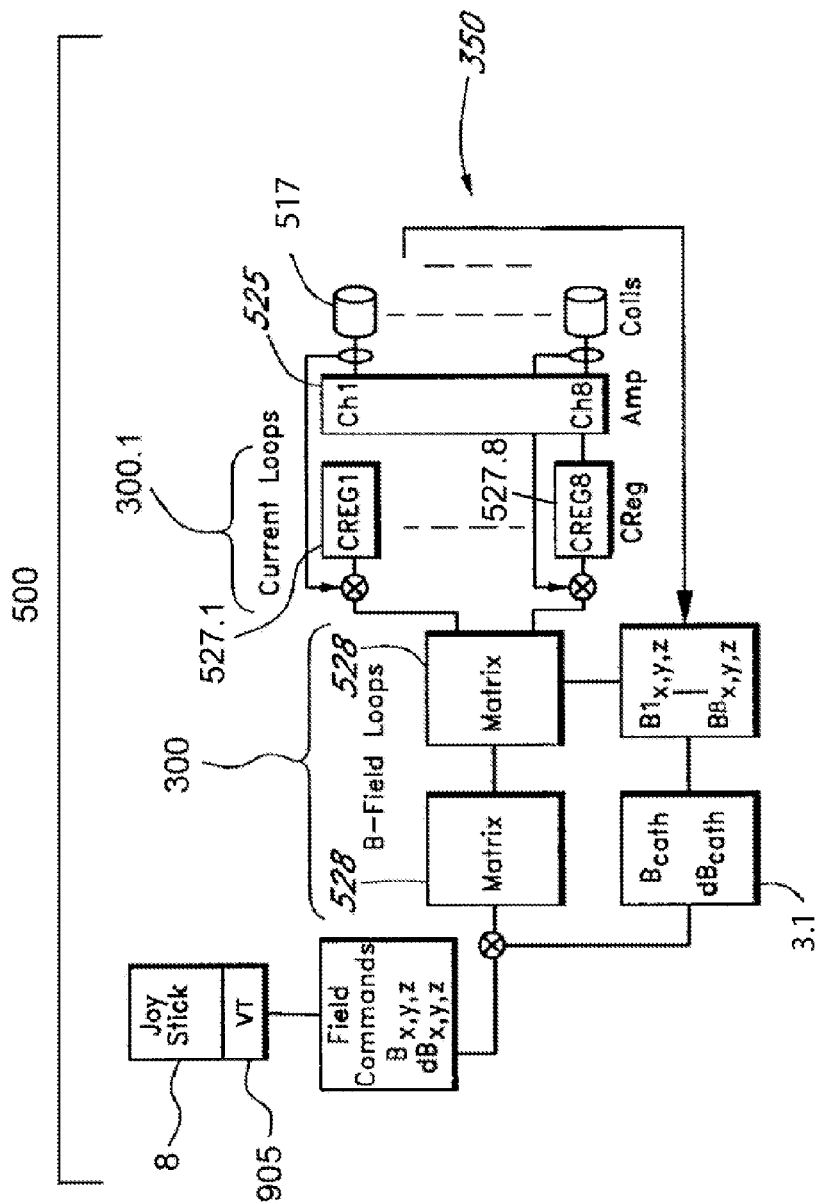
FIG. 9 is a block diagram of the CGCI regulator with its functional blocs.

FIG. 1B is a block diagram of the catheter guidance control and imaging system 15 used to guide the catheter 3.2 into tissue contact, by employing a virtual tip user input device (VT) 905 (seen in FIG. 9). In this embodiment, the catheter guidance control and imaging system 15 is the CGCI magnetic guidance system as described in U.S. patent application Ser. No. 11/697,690, Shachar et. al., "Method and Apparatus for Controlling Catheter Positioning and Orientation", Apr. 6, 2007 which is incorporated herein by reference in its entirety. The position detection and tissue contact detection system 7, such as the St. Jude Medical EnSite NavX system, sends the actual position (AP) of the catheter tip 3.1 and its associated tissue contact impedance signal (ECI) to the CGCI regulator 15 which accepts commands to either guide the catheter tip from the AP to a desired position (DP) 3.6, or to retract the catheter tip 3.1 from tissue contact. An automated mapping location sequence 10 sends the DP 3.6 through a series of target locations one at a time until the entire automated mapping targeting sequence 10 has been completed. The CGCI regulator 15 calculates a set of coil currents to shape the magnetic field within a CGCI waveguide 15.1 that will incrementally adjust the AP on a tissue contacting path through the DP 3.6 until continuous tissue contact is made. A magnetic field regulator 15.2 maintains these currents. In this embodiment, a catheter impedance seeking device 11 is also used which is described in U.S. patent application Ser. No. 12/323, 231, Shachar et. al, "System and Method for a Catheter Impedance Seeking Device", of Nov. 25, 2008 which is incorporated herein by reference in its entirety. The catheter impedance seeking device (CISD) 11 advances or retracts the catheter in synchronization with the CGCI regulator 15 and monitors the ECI tissue contact signal until continuous contact has been made over the desired number of heartbeats, such as to provide a repeatable level of continuous contact with the moving tissue surface that passes through the static geometric location DP 3.6.

Figure 2:
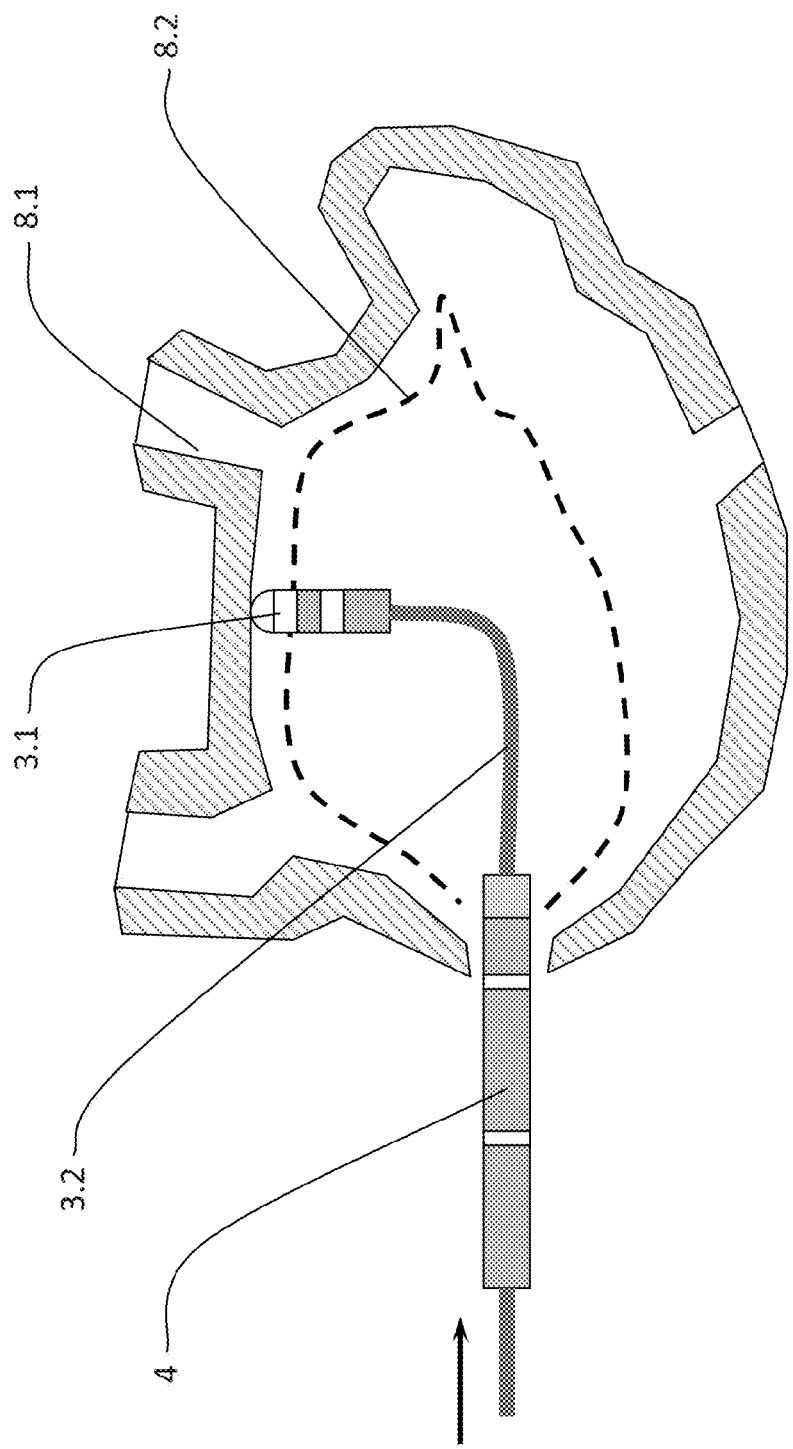
FIG. 2 is a cross sectional view of a coronary left atrium showing the regions of partial and continuous tissue contact with a catheter.

FIG. 2 is an illustration of a coronary left atrium depicting regions of partial and continuous tissue contact. Typically, a geometric shell is generated by a cardiac mapping system is at the extreme limits of catheter tip 3.1 travel. The supplemental tissue contact data guarantees that this geometric shell is a continuous contact manifold 8.1. A secondary zone within the chamber is mapped to define where intermittent tissue contact occurs. This partial contact zone 8.2 specifies a region where the catheter tip 3.1 has enough freedom of movement to adjust its position before re-seeking continuous contact. The catheter line 3.2 is advanced into the chamber 1.1 through the introducer sheath 4. The tissue contact sensing is provided at the catheter tip 3.1. The tissue contact is monitored over a user-selectable duration to differentiate between continuous and intermittent contact, and this information supplements the data received from the position detection and tissue contact sensing unit 7.

Figure 3:
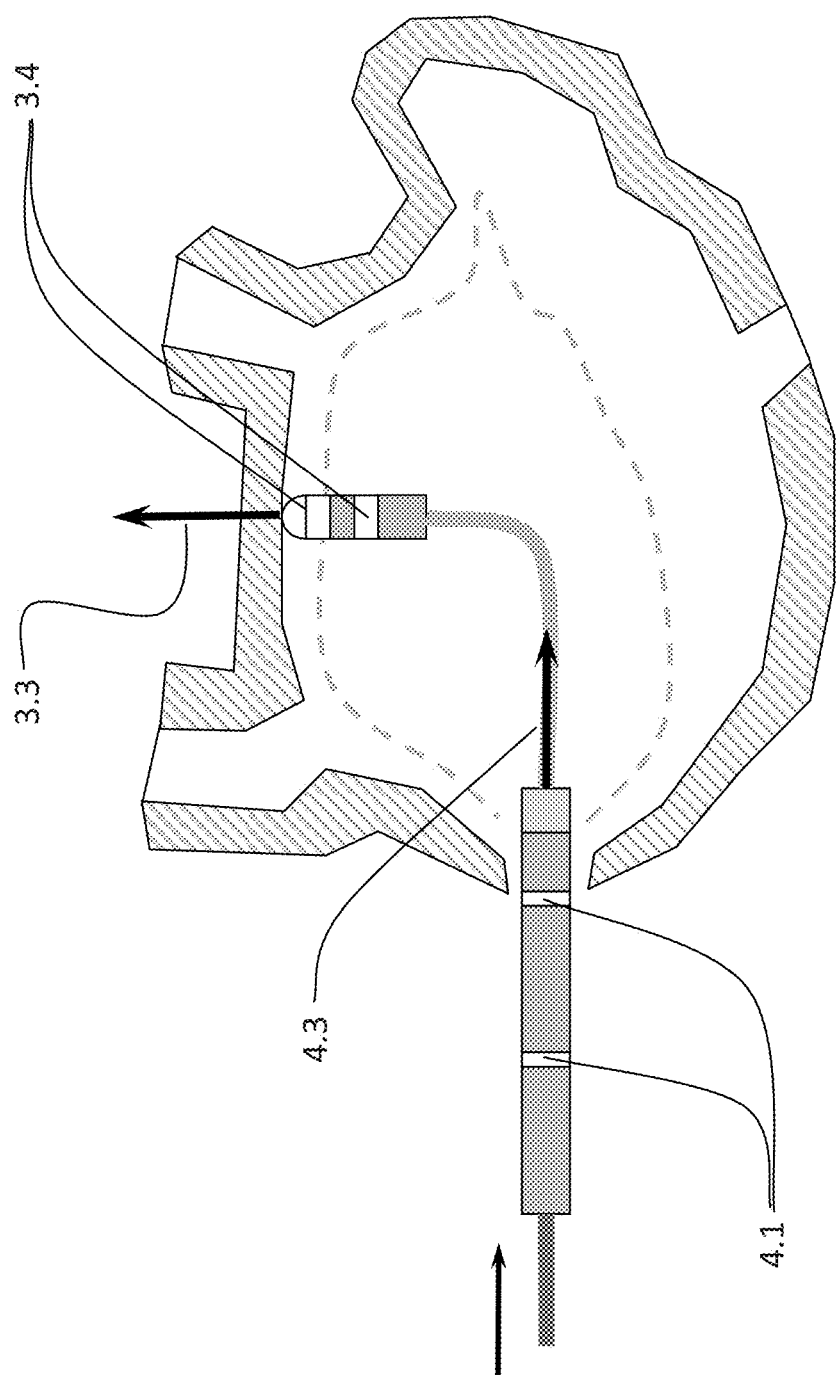
FIG. 3 is a cross sectional view of a coronary left atrium showing the position control reference vectors used in defining an automated mapping search pattern for a catheter.

Turning to FIG. 3, an illustration of a coronary left atrium is shown with the position control reference vectors used when defining an automated mapping search pattern. The catheter tip orientation 3.3 is determined from a plurality of catheter tip position detection electrodes 3.4 disposed on the catheter tip 3.1. The introducer sheath orientation 4.3 is determined from the sheath position detection electrodes 4.1. The desired position (DP) 3.6 is a Cartesian location coupled with a targeting direction that is used to regulate the actual position (AP) 3.5 of the catheter tip 3.1 on a path towards or though DP 3.6 until continuous tissue contact is made for a specified number of heartbeat cycles or fixed time duration.

Figure 4:
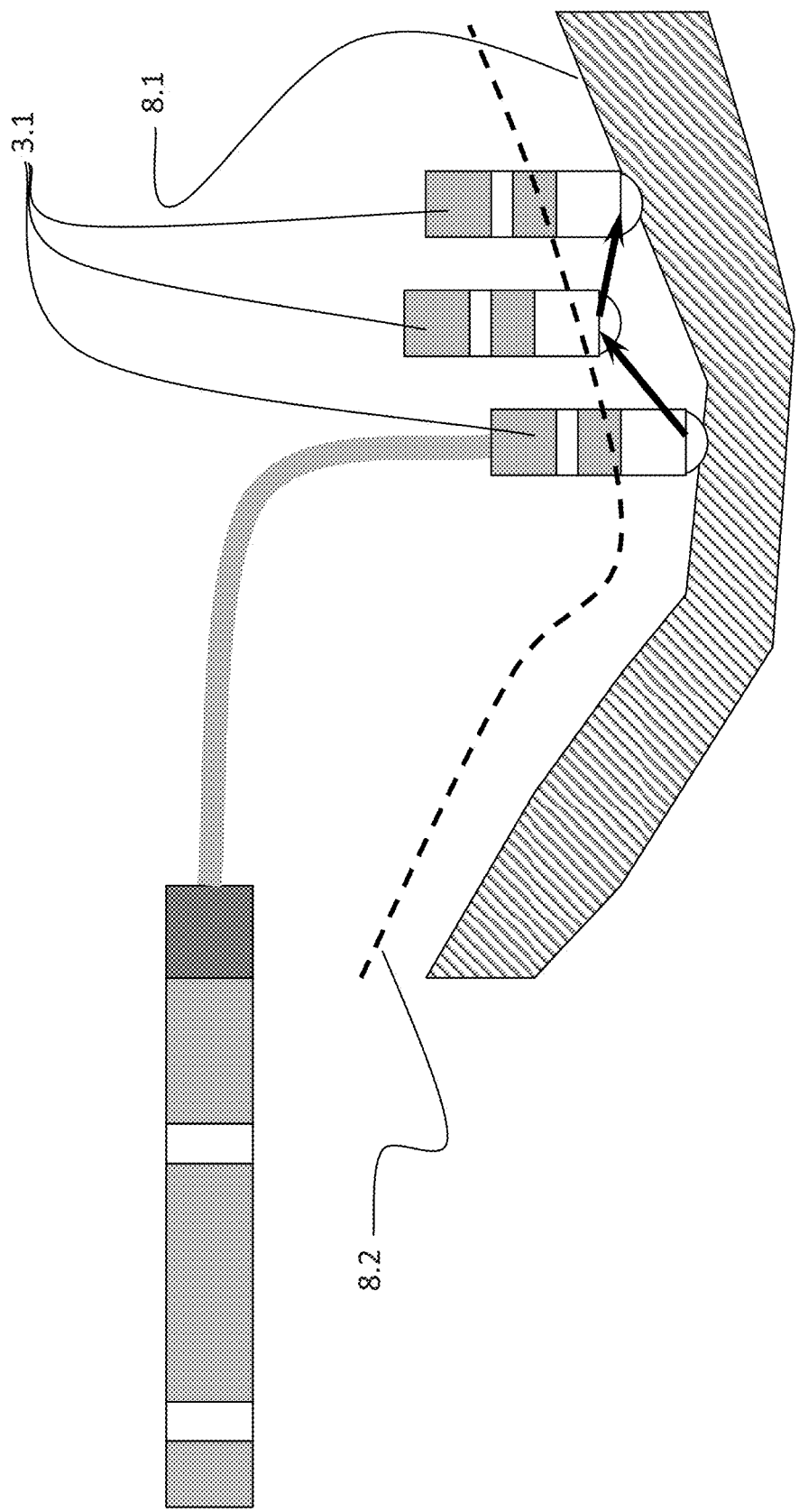
FIG. 4 is a magnified view of the catheter movement pattern used in the mapping of a coronary chamber.

FIG. 4 is a magnified view of a catheter movement pattern used in mapping a coronary chamber. The catheter tip 3.1 is moved from continuous contact with the tissue surface at DP1 3.6 on the continuous contact manifold 8.1 to a partial contact within the partial contact zone 8.2 while adjusting to the new position. A new position DP2 3.6 is then targeted without leaving the region between the continuous contact manifold 8.1 and the partial contact zone 8.2 so as to reduce the travel time and distance while mapping the continuous contact manifold 8.1.

Figure 5:
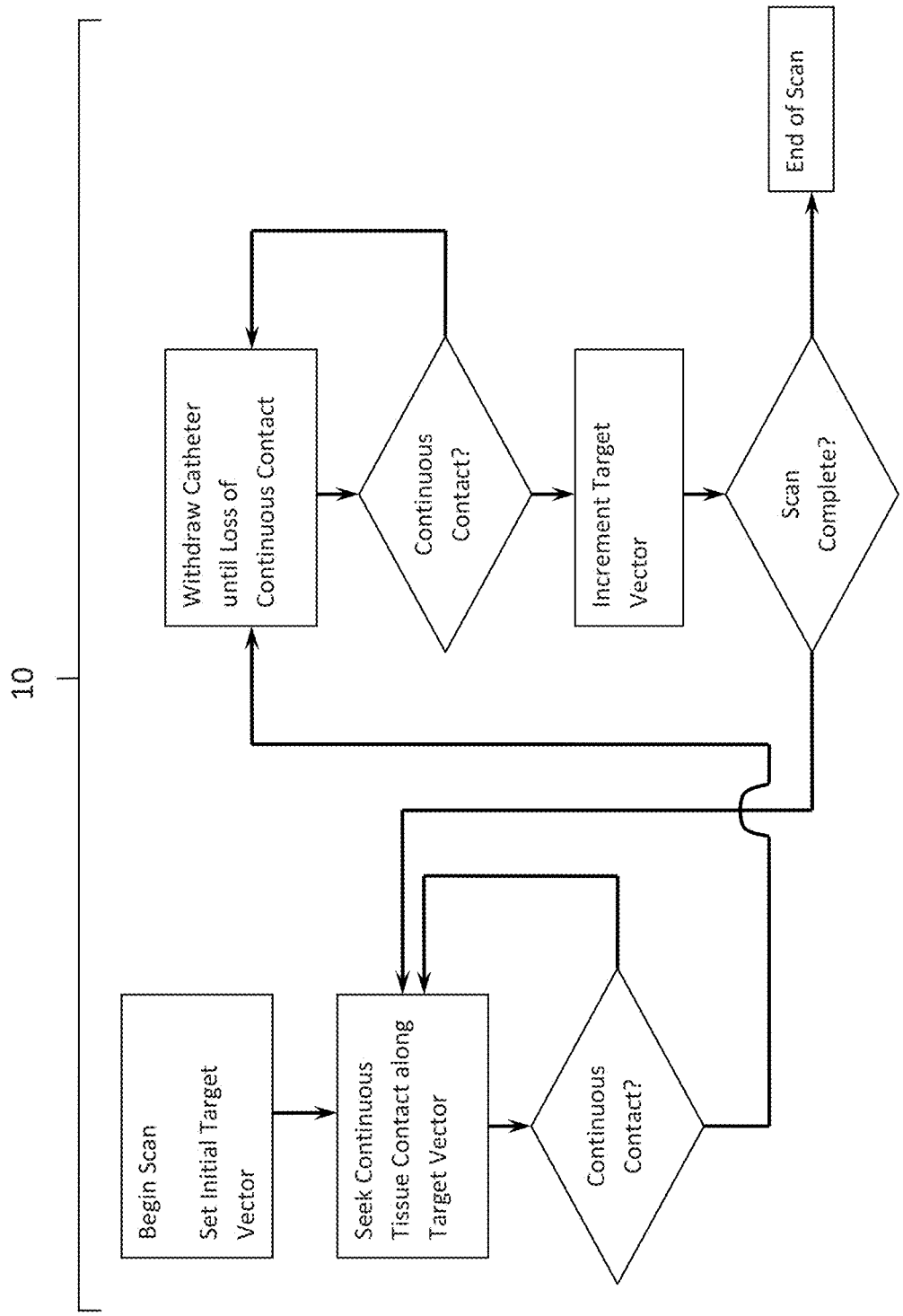
FIG. 5 is a flowchart of the command pipeline used by the catheter guidance control and imaging system during an automatic mapping procedure.

FIG. 5 is a flowchart of the command structure used by the catheter guidance control and imaging system 15 during an automatic mapping procedure. In this embodiment of the invention, an automated mapping routine 10 sends a series of target locations and retraction commands to the catheter position guidance and control unit 15 as seen in FIG. 1. After the routine has been started 10, and an initial target location has been set, the catheter 3.2 is manipulated along a target vector by the catheter guidance control system 15 to obtain continuous contact with that initial target location. If continuous contact has not been obtained at the initial target location, the catheter guidance system 15 continues to manipulate the catheter 3.2 until continuous contact is made. Once it is determined that continuous contact has been made at the target location, the catheter 3.2 is retracted until the continuous contact is lost. At this point, a new target location is acquired and the catheter guidance system 15 sends the catheter 3.2 along a new target vector to the new target location. The process of obtaining continuous contact described above is then repeated, with the catheter 3.2 being withdrawn every time improper contact has been made, until an entire location set has been acquired. If the user is satisfied with the acquired data received from the catheter 3.2, the scan is considered complete and the automated mapping procedure ends. If the user is not satisfied with the acquired data or if new target locations are added to the catheter guidance system 15, the catheter 3.2 is then taken through the entire process again from the beginning.

Figure 6:
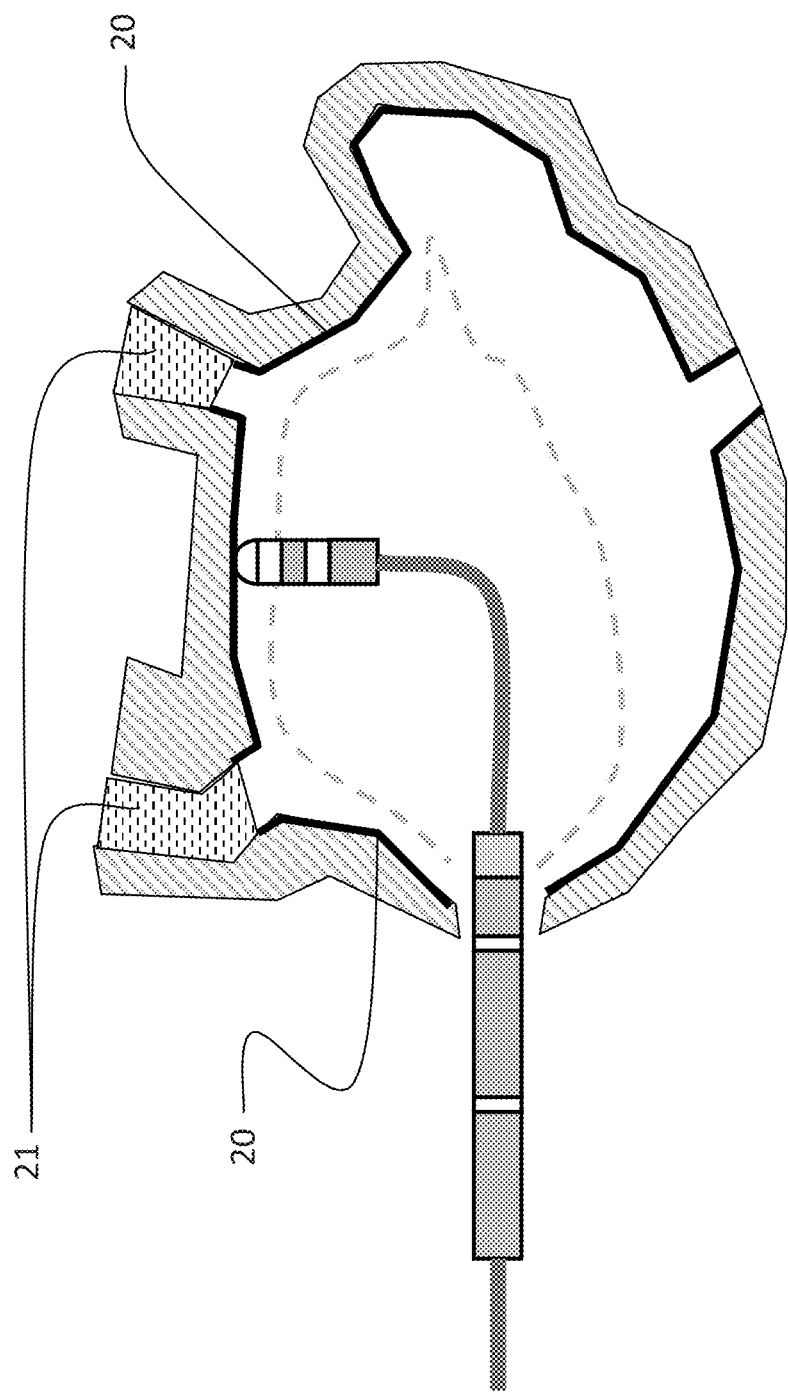
FIG. 6 is a cross sectional view of the use of tissue contact impedance values obtained by the catheter to differentiate between coronary wall tissue and vascular tissue.

FIG. 6 is a cross sectional view of how the catheter 3.2 uses obtained tissue contact impedance values to differentiate between the tissue of a coronary wall 20 and a vascular tissue 21. Two tissue types are illustrated to divide the geometric map into chamber tissue 20 and vascular tissue 21. The type of tissue at every DP may be recorded and then added to the geometric map in order to further supplement the automated mapping process. In other embodiments, the automated mapping algorithm may differentiate between tissue types other than what is listed here which can be differentiated by their dynamic impedance, including excitable tissue, scar tissue, valve tissue, etc. Each tissue type can be used to automatically generate a different mapping point density in a search algorithm, based on the level of medical significance.

Figure 7A:
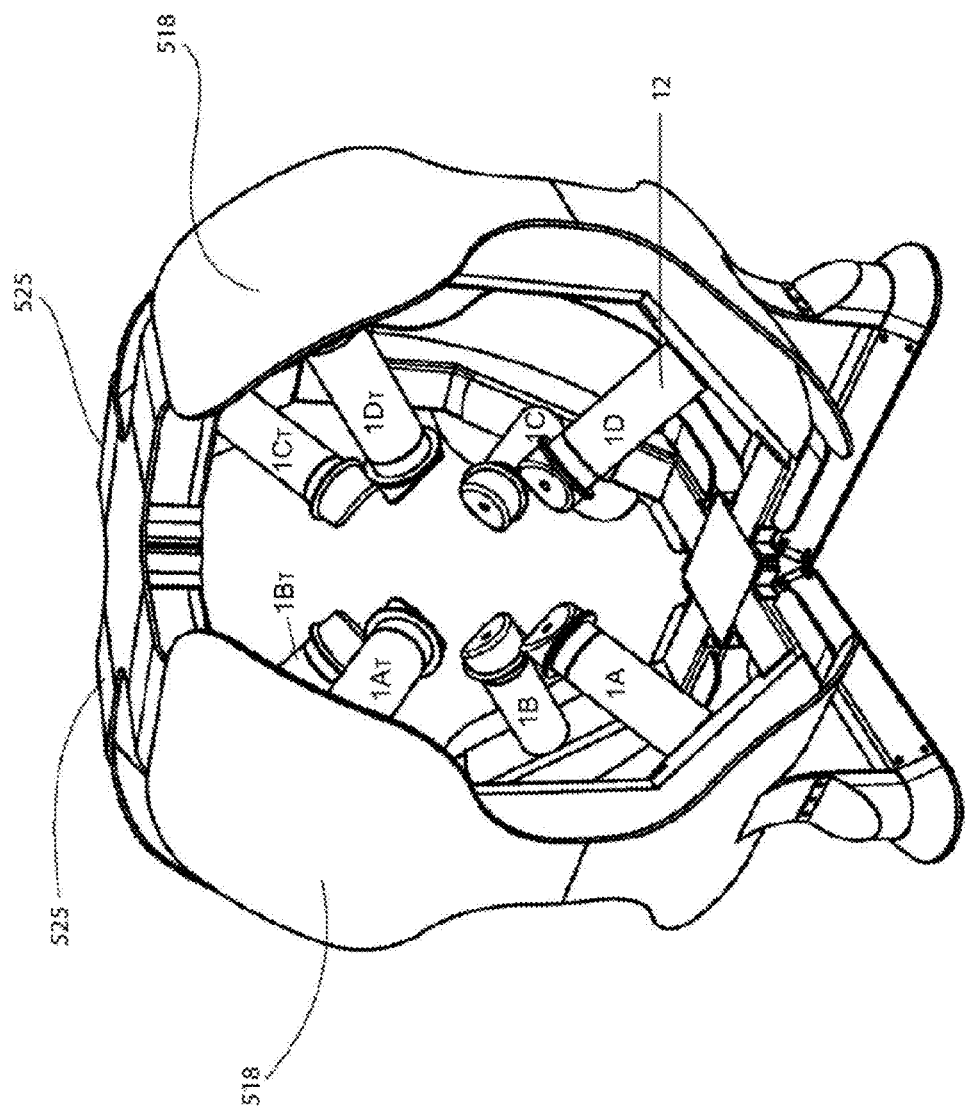
FIG. 7A is a perspective view of the CGCI waveguide system with the electromagnetic coils removed.
Figure 7B:
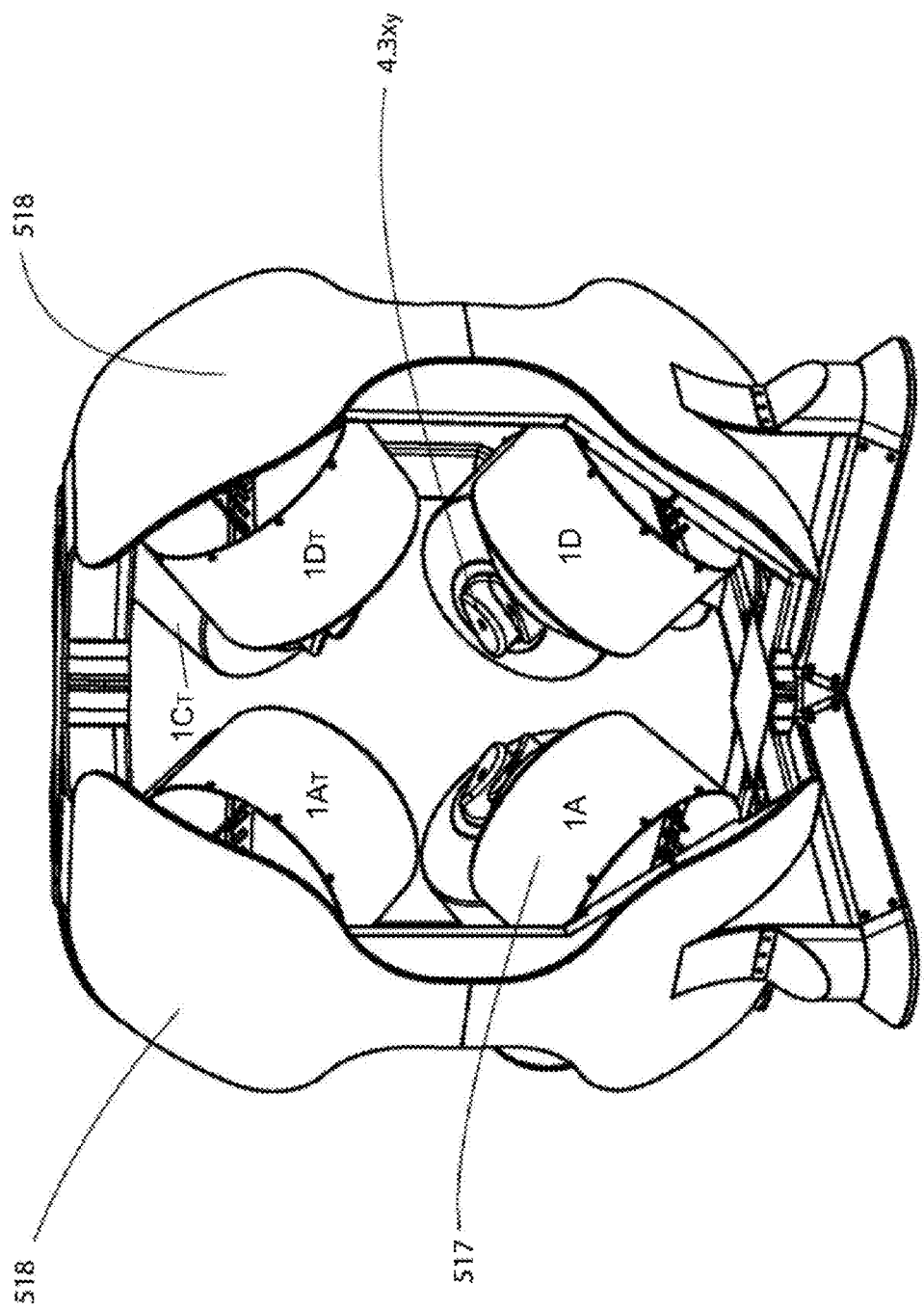
FIG. 7B is a perspective view of the CGCI waveguide system shown in FIG. 7A with the electromagnetic coils installed.
Figure 10:
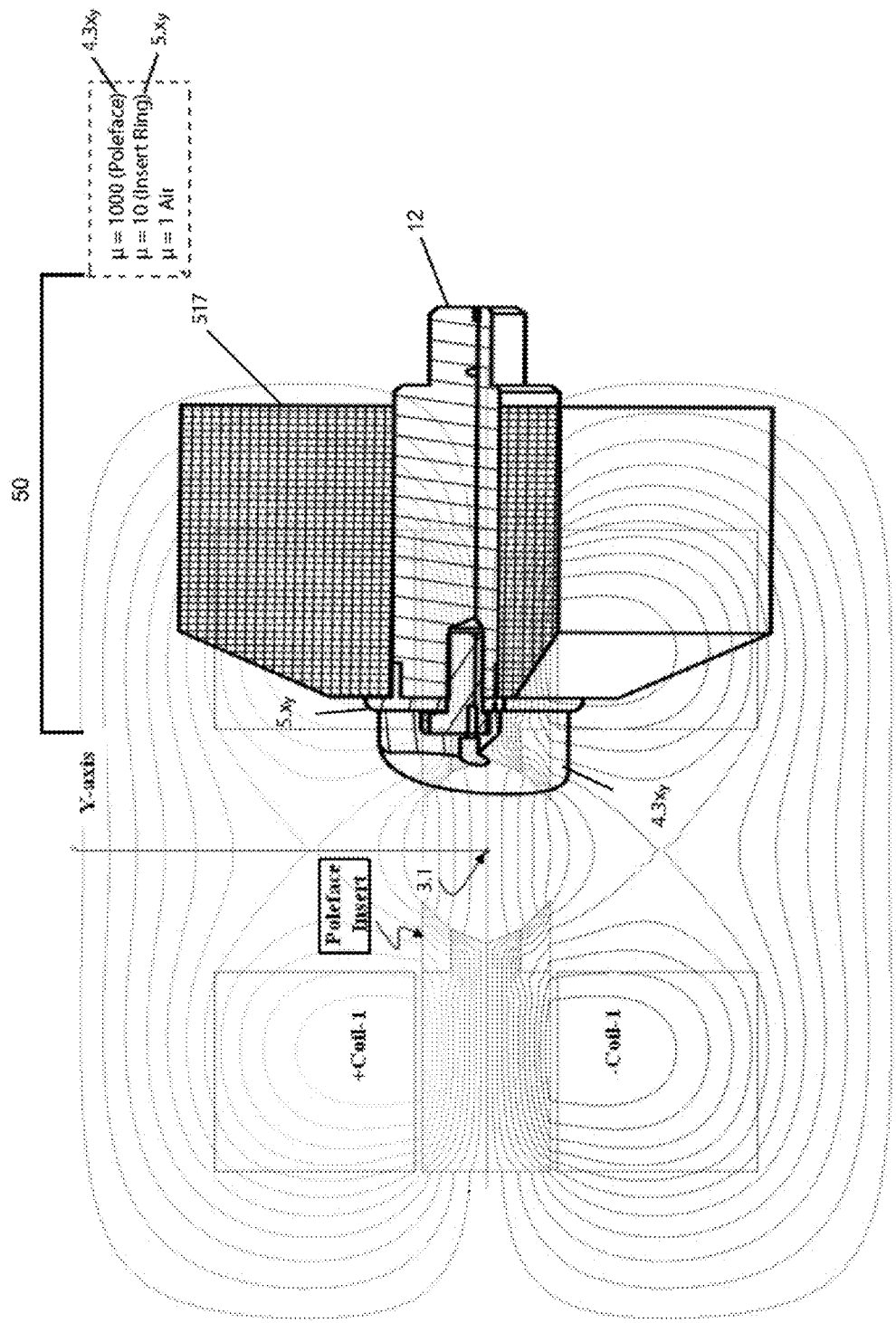
FIG. 10 is an orthographic cross section of the magnetic aperture (Lens) and its EM radiator of the CGCI.

FIGS. 7A-7C are perspective views of the CGCI waveguide 15.1 and its preferred embodiments. Turning to FIG. 7A, an isometric view of the CGCI waveguide 15.1 and its construction comprising a plurality of cores 12. In FIG. 7B a plurality of electromagnetic coils 517 are coupled to the core 12. Also seen in FIGS. 7A and 7B are the relative orientations of the polefaces $4.3x_y$ disposed on the distal end of each of the plurality of cores 12. The orientations of the poleface $4.3x_y$ are determined by the performance of electromagnetic radiation under Maxwell formalism and as modified by the wave equation for forming a shaped field 400 as described in further detail in Example 1 below. The combination of the core 12, electromagnetic coil 517, poleface $4.3x_y$ as well as a ring insert $5.x_y$ form a magnetic aperture 50 as best seen in FIG. 10.

The resulting effects of the CGCI waveguide 15.1 is to enable the apparatus to generate magnetic field geometries on demand, while shifting the magnetic flux density axis based on the AP to DP travel path of the catheter 3.2. It can also be seen in FIGS. 7A-7C the relative locations of a plurality of parabolic antenna shields 18 that are disposed around a magnetic circuit return path ferrous skeleton 525. The skeleton 525 preferably comprises at least four segments forming a substantially spherical chamber. Each of the cores 12 holds a coil 517 in the structure of the CGCI waveguide 15.1. Each of the upper coils 517, specifically coils 517 labeled $1A_T$, $1B_T$, $1C_T$ and $1D_T$ in FIG. 7B are held in place by their respective cores 12, specifically cores 12 labeled $1A_T$, $1B_T$, $1C_T$ and $1D_T$ as seen in FIG. 7A. The specific structure and the orientation of the cores 12 relative to a central axis of the CGCI 15.1 are determined in accordance with the spherical topology of the CGCI 15.1 which provides linear solutions to the location of the catheter tip 3.1. The spherical topology of the CGCI 15.1 further establishes the computing regimen necessary to solve a series partial differential equations as is known in the art by a regulator 500 seen in FIG. 8. These and other properties associated with the spherical topology are essential to the embodiments of this invention, as it enables the formation of anisotropic EM wave propagation without the customary non-linear representation of the fields, which can result in the inefficient and time consuming use of numerical as well a finite element (FEA) modeling of the field instead of the use of an analytical model as in the current invention.

FIG. 7C further illustrates the CGCI waveguide 15.1 and its eight coils 517 clustered and covered with the plurality of parabolic antenna shields 518. The performance of the CGCI waveguide 15.1 is enhanced by the use of parabolic shields 518 because any stray magnetic flux that is radiated above and beyond the effective boundaries of the assembly footprint are prevented from escaping and thus improving the efficiency of the CGCI waveguide 15.1.

Figure 8:
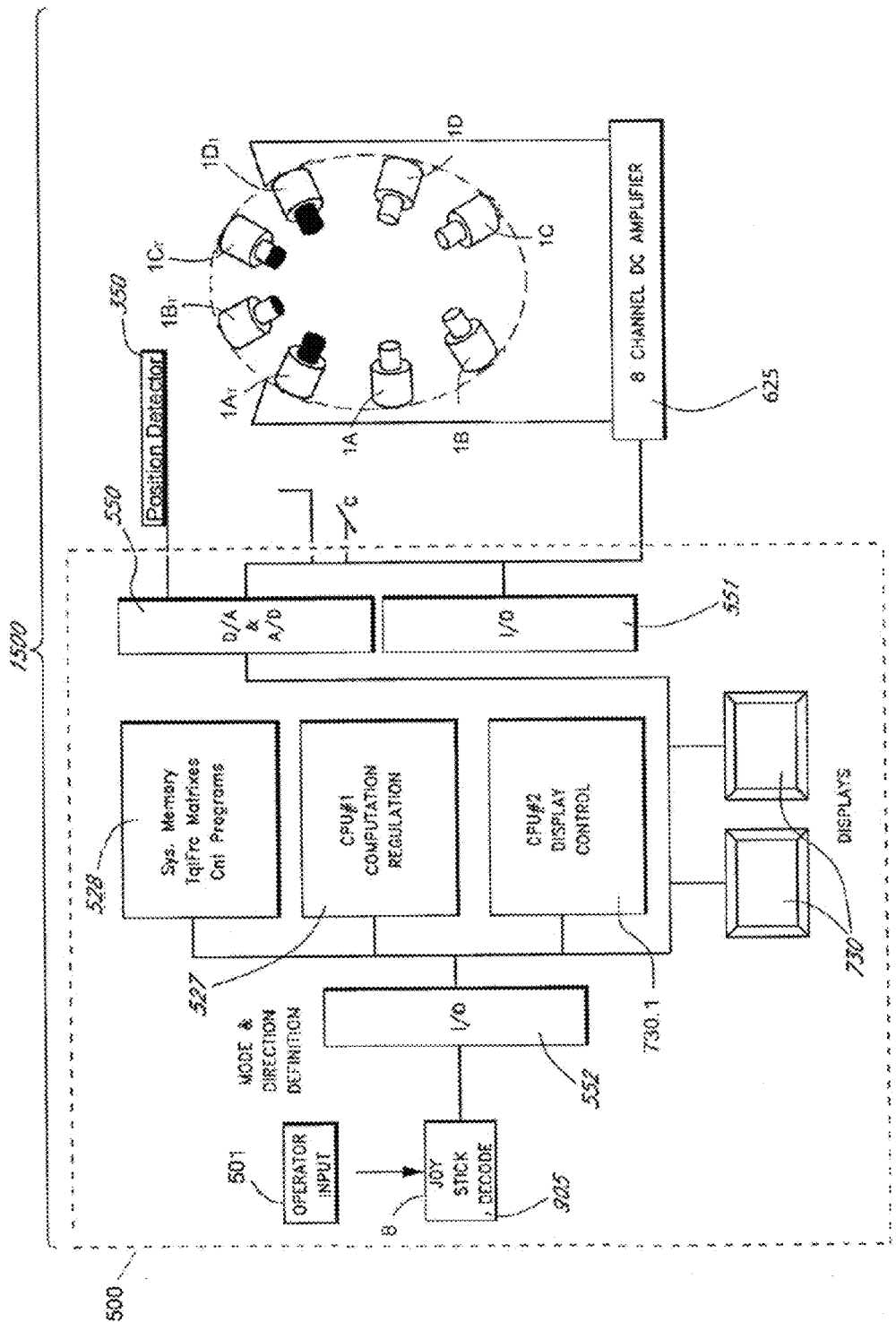
FIG. 8 is a block diagram of the CGCI functional elements.

FIGS. 8 and 9 are two possible configurations of a regulator scheme employed by the CGCI regulator 15 comprising a command circuit 500 used to perform the tasks of moving a catheter tip 3.1, from an AP 3.5 to a DP 3.6 with the necessary accuracy for delivering a medical tool in vivo. The command circuit 500 receives a command signal from an operator input 501, a position detector 350, a joy stick 8, and a virtual tip user input device (VT) 905 contemporaneously. The command circuit 500 then determines a new DP 3.6 from the data obtained by generating a Bx, By, Bz vector for torque control, and the dBx, dBy, dBz vector gradient for force control. With these position values identified, the command circuit 500 is allowed to receive two sets of field values for comparison.

The present value of the AP 3.5 and of the Bcath and dBcath 300 acting on the catheter tip 3.1 seen in FIG. 9, are calculated from the position detector 350 and outputs B x, y, z. The new field values for the DP 3.6 (Bx, By, Bz, dBx, dBy, dBz) are used to advance the catheter tip 3.1 and are generated in the command circuit 500 with the help of a customary D/A A/D 550, a set of IOs 551, 552, and a set of display controls 730, 730.1. The difference in the AP 3.5 and the DP 3.6 is translated to a matrix block 528 for setting the coil currents 300.1 and polarities within the electromagnetic coils 517 and cores 12 respectively.

In one embodiment the matrix block 528 issues a plurality of current reference signals to a set of eight regulators (CREG) 527 seen in FIG. 9. It is preferred that eight separate CREG units 527 be used so that they may individually respond to the needs of the path translation or rotation from AP to DP within each of the coils 517, however fewer or additional CREG units 527 than what is shown may be used without departing from the original spirit and scope of the invention. The command circuit 500 drives an eight-channel power amplifier 625 to obtain the desired currents within the coils 517.

Figure 11:
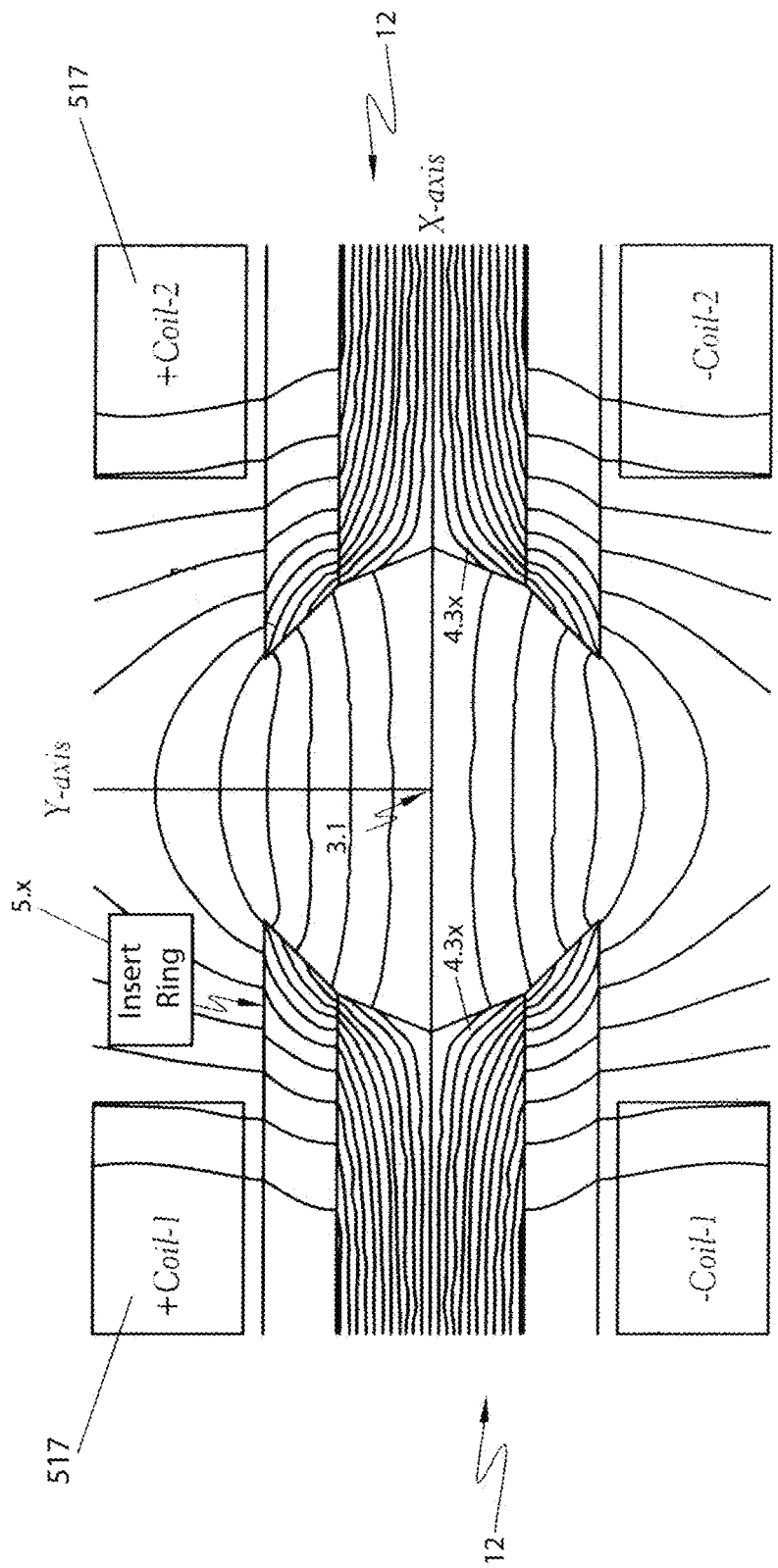
FIG. 11 is a schematic representation of the flux line geometry due to the refraction index generated by a magnetic aperture (the Lens) of the CGCI.
Figure 12:
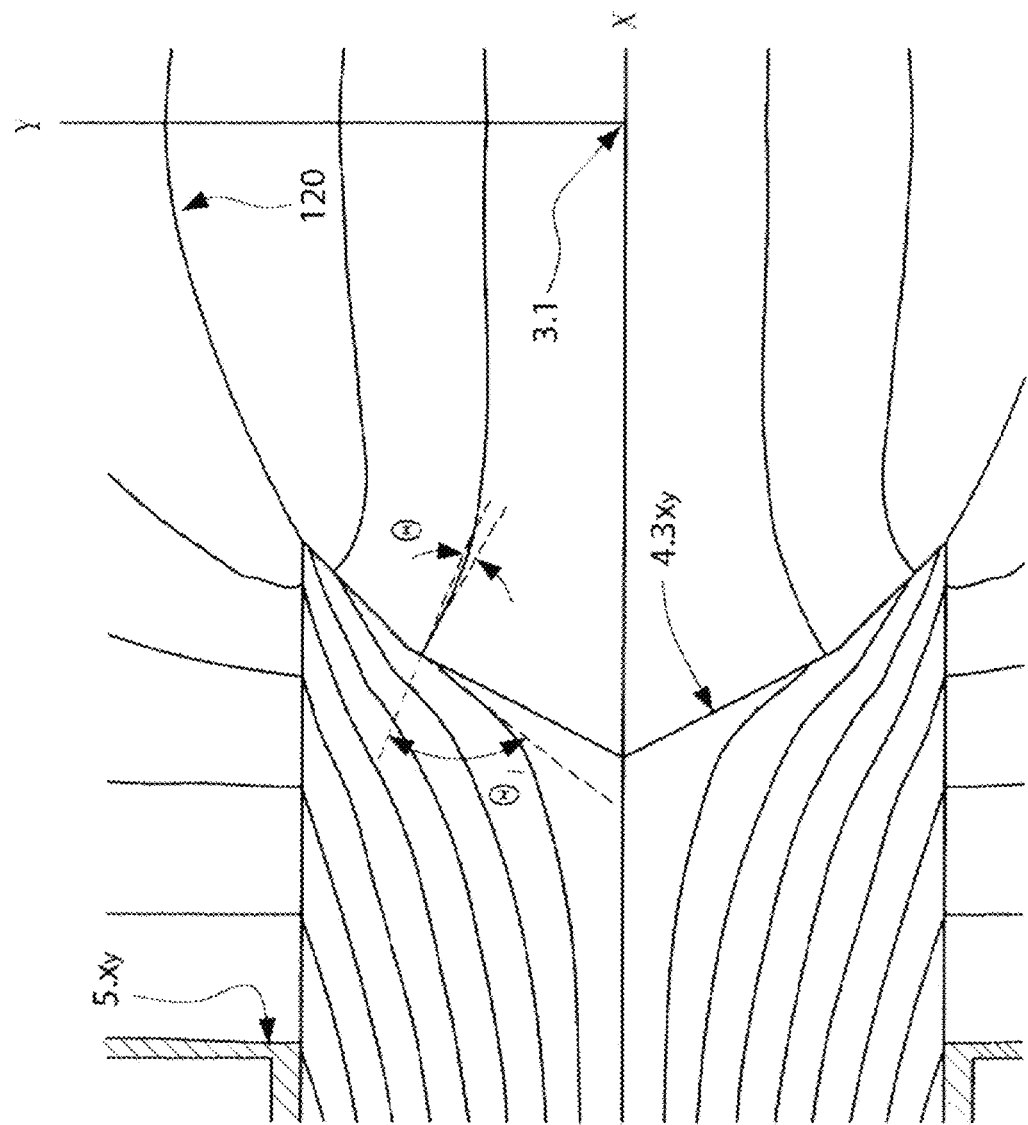
FIG. 12 is a sectional view of the lens demonstrating its efficiency as described by the computational schema.

FIGS. 10-12 are schematic cross sections of the magnetic aperture 50 that forms a magnetic shaped field 60 seen in FIGS. 13A-13C. The magnetic aperture 50 comprises a coil 517 and a core 12. The core 12 is comprised of material such as ASTMA848 steel with material permeability with a value set of $\mu > 1000$. The poleface $4.3x_y$ is fitted with an insert ring $5.x_y$ which is fitted over the poleface $4.3x_y$ as shown in FIG. 10. The insert ring $5.x_y$ is comprised of material such as 1010 steel with a value set of $\mu > 10$.

FIGS. 10-12 further elaborate on the preferred embodiments of the configured waveguide 15.1. FIG. 10 illustrates the formation of the magnetic aperture 50. The physical principle that governs the effects associated with shaped electromagnetic radiation and which establishes a lens 120, is the discontinuity of material properties, such as the permeability ($\mu > 1000$) of the ferrous materials used in the core 12 and the poleface $4.3x_y$ ($\mu > 10$) coupled with the insert ring $5.x_y$ which has a permeability value of $\mu = 10$ and as contrasted with the permeability value of air ($\mu > 1$). The above permeability combinations generate a step change that is representative of the refractive angle at the boundaries. As the magnetic flux leaves the ferrous material of the core 12, poleface $4.3x_y$, and insert ring $5.x_y$, they enter the operating region of air with a permeability value of $\mu > 1$. A magneto-optical transition is present within the operating region which attenuates the localized minimums of the magnetic field vector which have been long been used in the prior art for example with current carrying structures used in plasma physics, particle trapping, and levitation. Large currents are required in the prior art techniques, however applying the lens 120 of the current invention avoids the need to create such currents. The lens 120 of the current invention provides a favorable alternative that can be used, for example, in confining the flux density axis relative to the catheter tip 3.1 so as to push, pull, and rotate the catheter tip 3.1 on demand without the customary current noted by the prior art.

Figure 12A:
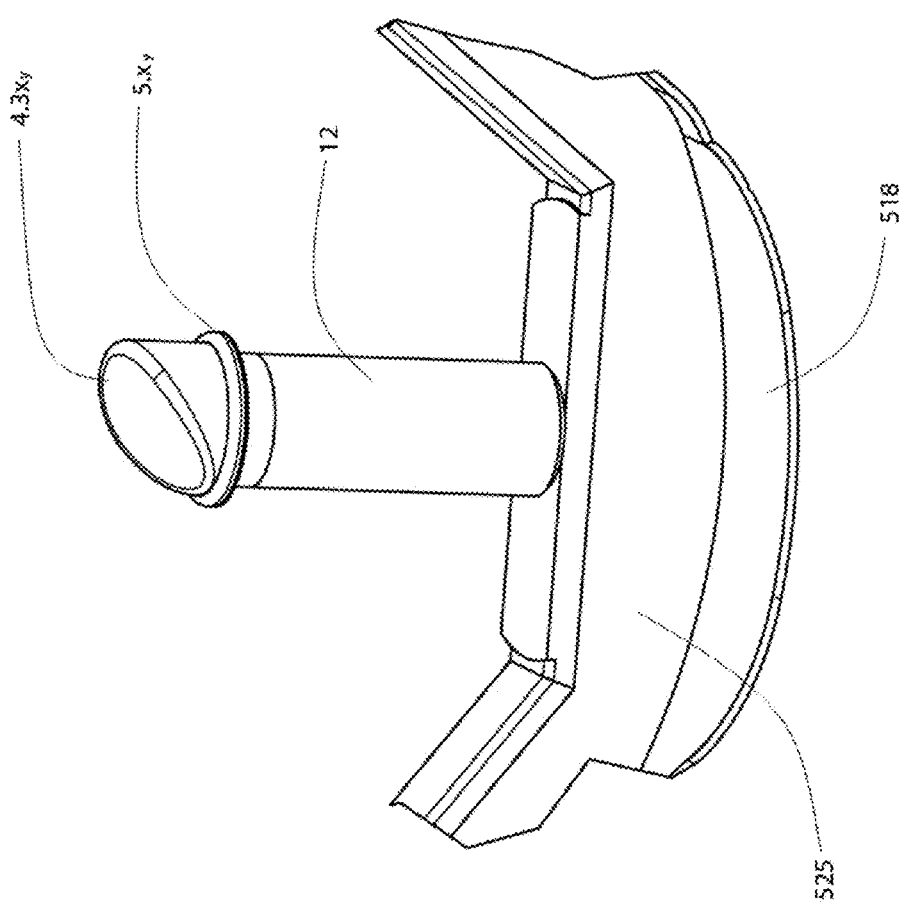
FIG. 12A is a perspective view of the magnetic aperture of the CGCI and its adjacent structure.

Turning now to FIG. 12A, an orthographic representation of the magnetic aperture 50 and its adjacent structure comprising of the poleface $4.3x_y$ and the insert ring $5.x_y$ supported by the core 12 is shown. The entire assembly forms a lens 120 which employs the permeability difference. A detailed description of the operation of the lens 120 is described by the example noted below.

FIGS. 13A-13C are top view schematic representations of the geometry of the magnetic fields produced by the CGCI waveguide 15.1 relative to the CGCI waveguide 15.1 assembly. The CGCI waveguide 15.1 in one preferred embodiment as disclosed above consists of eight electromagnets 517 positioned symmetrically about a substantially spherical magnetically conductive ferrous skeleton 525 such that each core 12 faces the other seven cores with a symmetrical physical perspective. Thus, each of the electromagnets 517 occupies a segment of the enclosing sphere with each segment angled at ±45° from the skeleton's 525 center coordinate system. There are no privileged positions for any of the electromagnets 517 in any direction relative to the center region which contains the catheter tip 3.1 to be positioned and oriented by the CGCI magnetic field 60.

Once the magnetic field 60 is generated by any number or combination of the eight electromagnets 517, the catheter tip 3.1 will experience a torque aligning it to the direction of the field and a force moving it along the field's gradient. The magnetic flux generated by a single electromagnet 517 will close through all the other seven cores 12 due to the spherical symmetry of the cores 12 and the magnetic path available through the ferrous skeleton 525 which holds the magnetic aperture 50 assemblies together. An example of the direction of the magnetic flux and the distribution of the magnetic flux density is shown by the arrow seen in FIGS. 13A-13C. The flux density map will resemble a lobe shape field 60 seen in FIG. 13A, where the 'lobe' indicates an extension or projection of the magnetic field 60 generated by the source, namely the current density vector in the particular coil 517 shown.

The CGCI magnetic skeleton 525 comprises two circular armatures crossing each other at a 90° angle. This configuration situates each of the eight coils 517 on the inside surface of a virtual sphere where the magnetic skeleton 525 provides closed flux paths on six planes with four coils 517 each. The magnetic vector-plane, shown as a shaped lobe 60 in FIG. 13A, with all eight coils 517 in operation forms a 3D magnetic volume 60 shown in FIG. 13B with uniform torque-field and high gradient-force linearity. Each coil 517 is controlled independently, thus the magnetic vector direction, magnitude and slope offers 6 degrees of control freedom.

On the outside surface of CGCI ferrous skeleton 525 are a plurality of additional parabolic antenna flux shields 518 which shield the exterior area from parasitic magnetic fields escaping the CGCI waveguide 15.1 between the circular armature structures. The shields 518 are shaped such that any escaping flux lines are redirected onto a return path behind the coil 517 assemblies. The captured stray flux contributes to the internal flux density available at the center region and improves the overall shape of the shaped magnetic volume 60 as seen in FIG. 13C. Also shown in FIG. 13C, the paths of the stray flux lines, shown as broken line arrows, interact with the shields 518 installed on the ferrous skeleton 525 and reduce the stray magnetic fields at 5 feet from the surface of the CGCI waveguide 15.1 to a value of below 5 Gauss.

Utilizing the spherical symmetry described above, linearity and uniformity of the generated magnetic field 60 is achieved within the center region of the CGCI waveguide 15.1 which can be used to accurately and quickly advance the catheter 3.2 position and orientation via the command circuit 500. The closed loop guidance of the magnetically tipped catheter 3.1 is aided by real-time computing of a simple magnetic landscape of the changing fields and gradients within the interior of the lobe. The landscape is generated from the continuously measured magnetic boundary conditions at the polefaces 4.3$x_y$, and from the calculated field density vectors set by the current in the eight coils 517. Thus, the command circuit 500 having obtained the desired position 3.6 from the operator, will not only charter a path to the target based on the physical map of the endocardial surface, but will also integrate the information available from the magnetic landscape of the lobe. Knowing the magnetic landscape allows for the computation of the highest possible field intensity and gradient available at the actual position AP 3.5 with the catheter 3.2 in route to the target DP 3.6. This regulation technique complements the strictly location-based field generation and moves the catheter 3.2 in real-time at the maximum obtainable speed. In addition, the field-shaping performance is enhanced within the CGCI waveguide 15.1 with magnetic shields 518 capturing and reorienting stray magnetic fields and flux into the center region.

Magnetic lensing with poleface permeability refractors is accomplished by the CGCI waveguide 15.1 by use of the CGCI coils 517 which are disposed around a ferrous core 12 material with polefaces 4.3$x_y$ protruding into the center region. The poleface 4.3$x_y$ orientation is determined by pointing it toward the catheter tip 3.1 such that the rounded and raised end is pointed towered the catheter tip 3.1 and its highest generated flux density is directed towered the catheter 3.2 main axis. The current invention employs these magnetic focusing enhancements by using the general laws of electromagnetic wave propagation through materials of different dialectic and magnetic properties and as described by Snell's law of refraction. In its simplest form the law states that the relative angles of wave propagation in one media through the boundary of the second media depends on both the dielectric and magnetic properties of each media, jointly defining the index of refraction coefficient n(ω). The speed of the electromagnetic wave is given by c, thus the speed of magnetic wave propagation in the media is inversely proportional to the index of refraction. This index can be expressed in terms of permittivity $\epsilon(\omega)$ and permeability $\mu(\omega)$. The permittivity and permeability of the mediums are related to the index of refraction by the relation of $\mu(\omega) \cdot \epsilon(\omega) = n^2(\omega)/c^2$.

Snell's law states: $n_1 \sin(\theta_1) = n_2 \sin(\theta_2)$ In a static (ω≅0) magnetic structure we can write for the general relation:

$$\frac{B_{1t}}{\mu_1} = \frac{B_{2t}}{\mu_2}$$

if $J_s = 0$, where subscript 1*t* and 2*t* stands for the tangential components of B on both sides of the boundary. The tangential components of B are discontinuous regardless of any current density at the interface. This discontinuity is related to the permeability of the two mediums. As a direct consequence of the above interface conditions, the magnetic field (either H or B) is refracted at the interface between the two materials (magnetic steel, such as A858 with permeability $\mu_{steel}$=>1000 and air with permeability $\mu_{air}$=1). Rearranging and substituting we obtain $$\tan\theta_1 = \frac{H_{1t}}{H_{1n}} \text{ and}$$

$$\tan\theta_2 = \frac{H_{2t}}{H_{2n}}$$

where t stands for tangential component and n for normal component.

Substituting H=B/μ and $B_{1n}=B_{2n}$ we obtain $$\frac{\tan\theta_1}{\tan\theta_2} = \frac{\mu_1}{\mu_2}.$$

The above equations correspond to a common interpretation of relativistic wave propagation dynamics and its salient case of a non-relativistic static perspective. The static solution seen FIG. 12 calculates as follows:
ti $\theta_1=\lambda°$, $\mu_1-1000$, $\mu_2-1$, ps $$\tan\theta_2 = \frac{\mu_2}{\mu_1 \cdot \tan\theta_1},$$

thus $\theta_2 < 1°$

The resultant optical displacement associated with the discontinuity of the medium due to permeability difference between the poleface 4.3$x_y$ and insert ring 5.$x_y$ enable the formation of a lens 120 shown as flux line map in FIG. 12.

Figure 14:
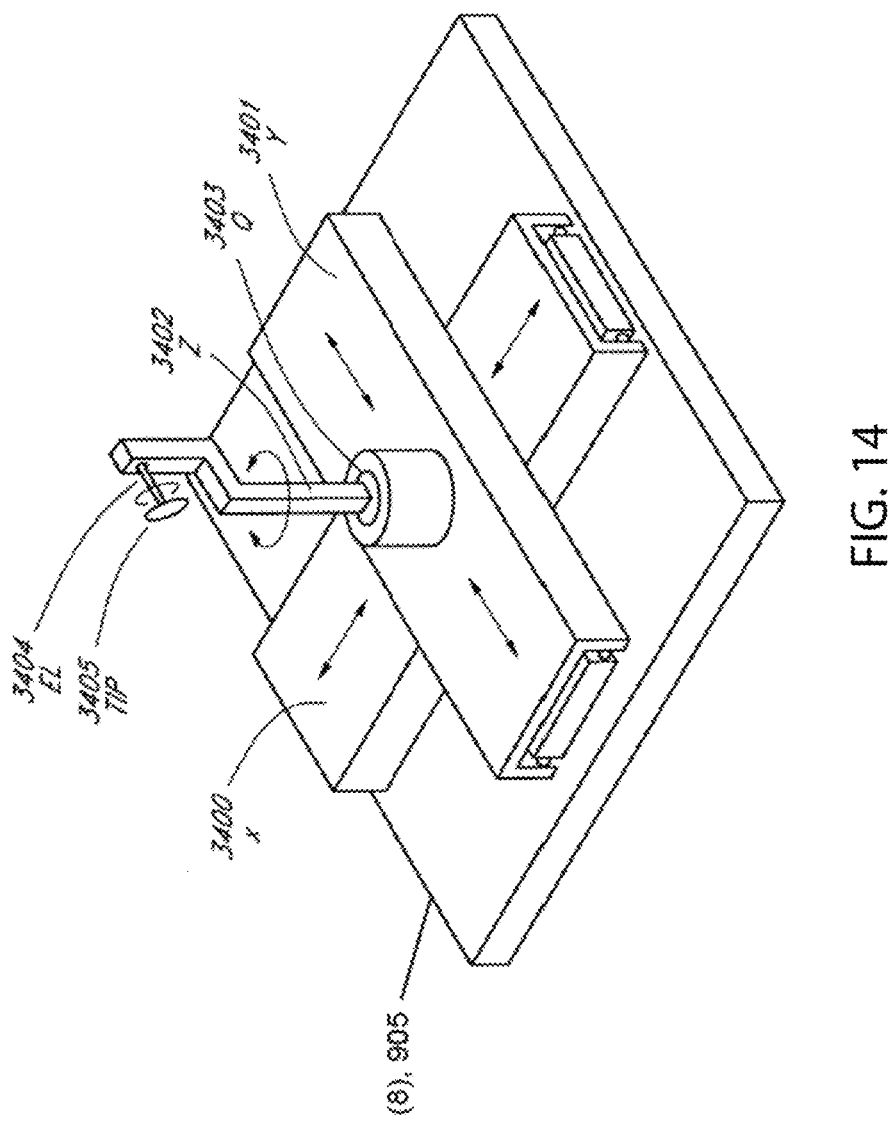
FIG. 14 is a perspective view of the Virtual Tip (VT) user input device.

FIG. 14 is a perspective view showing one preferred embodiment of the virtual tip user input device 905. The virtual tip 905 is a multi-axis joystick-type device which allows the surgeon to provide inputs to control the position, orientation, and rotation of the catheter tip 3.1, within the CGCI waveguide 15.1 chamber. In one embodiment, the virtual tip 905 includes an X-direction input 3400, a Y-direction input 3404, a Z-direction input 3402, and a phi rotation input 3403 for controlling the position of the catheter tip. The virtual tip 905 further comprises a tip rotation input 3405 and a tip elevation input 3404. As described above, the surgeon manipulates the virtual tip 905 and the virtual tip 905 communicates the surgeon's movements to the command circuit 500. The command circuit 500 then generates instructions for the proper currents 300.1 in the coils 517 to be produced and to effect motion of actual catheter tip 3.1 to follow the motions entered into the virtual tip 905. In one embodiment, the virtual tip 905 comprises various motors and/or actuators (e.g., permanent-magnet motors/actuators, stepper motors, linear motors, piezoelectric motors, linear actuators, etc.) to provide force feedback to the operator to provide tactile indications that the catheter tip 3.1 has encountered an obstruction or obstacle.

Figure 15:
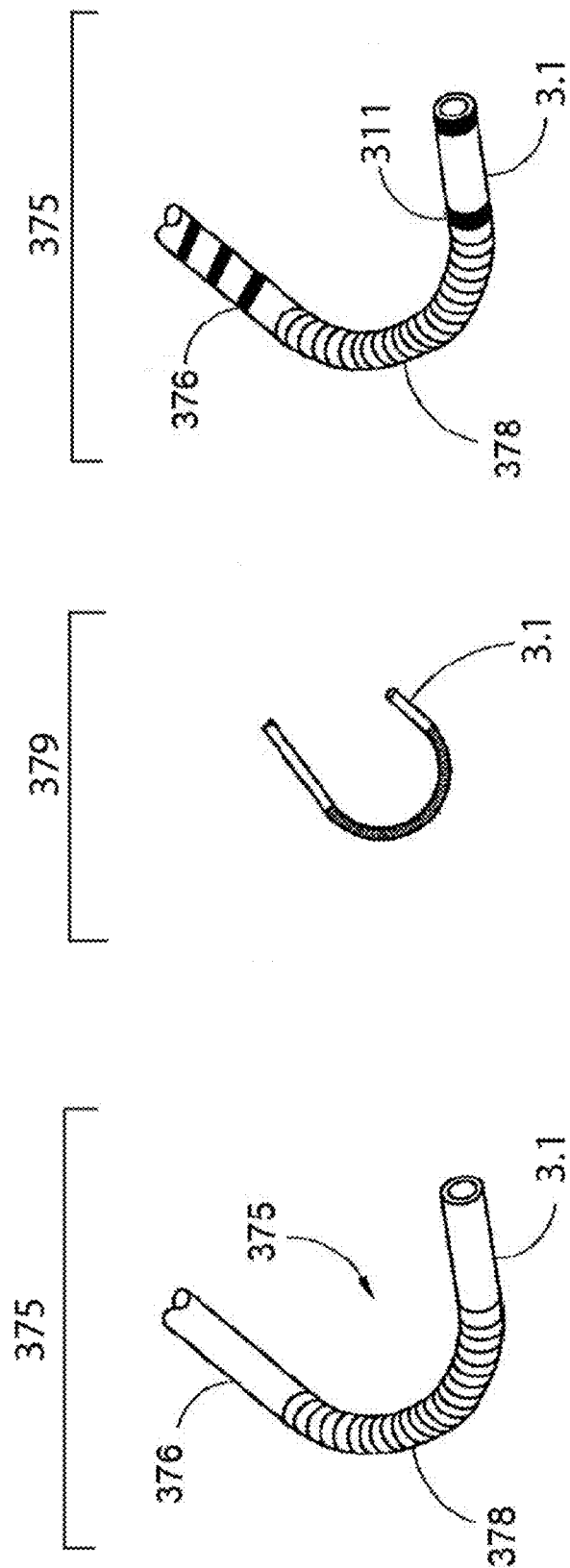
FIG. 15 is a perspective view of a catheter and a guide wire fitted with a magnetic pallet.

FIG. 15 is a representation of the medical tool(s) that may be controlled by the CGCI waveguide 15.1. Once such tool is a catheter 375 fitted with a permanent magnet 3.1 at its distal end. The catheter 375 further comprises a catheter body 376, which extends into a flexible section 378 that possesses sufficient flexibility for allowing the relatively more rigid responsive tip 3.1 to be steered through the patient's body 1. Alternatively, the catheter may comprise an articulated set of permanent magnets in the distal end of the tool.

In one embodiment, the catheter tip 3.1 includes a guidewire assembly 379 seen in FIG. 15 that is responsive to magnetic fields. The responsive distal tips 3.1 of both the catheter assembly 375 and the guidewire assembly 379 respectively, comprise a plurality of magnetic elements such as permanent magnets that respond to the external flux generated by the CGCI waveguide's 15.1 electromagnetic coils 517.

In one particular embodiment, the magnetic catheter assembly 375 in combination with the CGCI waveguide 15.1 reduces or eliminates the need for the plethora of medical tools normally needed to perform diagnostic and therapeutic procedures. During a conventional catheterization procedure, the surgeon often encounters difficulty in guiding the conventional catheter to the desired position 3.6, since the process is manual and relies on manual dexterity to maneuver the catheter 3.2 through a tortuous path of, for example, the cardiovascular system. Thus, a plethora of catheters in varying sizes and shapes have to be made available to the surgeon in order to assist him/her in the task since such tasks require different bends in different situations due to natural anatomical variations within and between patients. By using the CGCI waveguide 15.1 and while manipulating the distal magnetic element 3.1, only a single catheter 3.2 is needed for most, if not all geometries associated with the vascular or the heart chambers. The catheterization procedure is now achieved with the help of the CGCI waveguide 15.1 that guides the magnetic catheter 375 and/or a guidewire assembly 379 to the desired position 3.6 within the patient's body 1 as dictated by the surgeon's manipulation of the virtual tip 905. The magnetic catheter 375 and guidewire assembly 379 provides the flexibility needed to overcome tortuous paths, since the CGCI waveguide 15.1 overcomes most, if not all the physical limitations faced by the surgeon while attempting to manually advance the catheter tip 3.1 through the patient's body 1.

In another embodiment, the responsive tip 3.1 of the catheter assembly 375 is substantially tubular in shape and is a solid cylinder. The responsive tip 3.1 of the catheter assembly 375 is a dipole with a longitudinal polar orientation created by the two ends of a magnetic element positioned longitudinally within it. Similarly, the responsive tip 3.1 of the guidewire assembly 379 is a dipole with a longitudinal polar orientation created by two ends of the magnetic element 3.1 positioned longitudinally within it.

In another embodiment, a high performance permanent magnet is used in forming the distal end 3.1 of the catheter assembly 375 so as to simultaneously have a high remanence $M_r$, a high Curie temperature $T_c$, and a strong uniaxial anisotropy. The high performance permanent magnet in the distal tip 3.1 preferably comprises a coercive field $H_c$, (defined as the reverse field required to reduce the magnetization to zero) and a $(BH)_{max}$ that are inversely proportional to the volume of permanent magnet material needed to produce a magnetic field in a given volume of space.

FIG. 15 also shows an alternative possible formation of a catheter assembly 375 whereby the permanent magnet in the distal tip 3.1 is supplemented with additional set of small beads 311. The magnet in the distal tip 3.1 and the beads 311 are fabricated using magnetic materials and chemical compositions having at least two different $H_c$ values which enable a formation of a universal joint as is known in the art. The magnetic field B emanating from the CGCI waveguide's 15.1 electromagnetic coils 517 is applied uniformly onto the axial magnetization of the magnetic tip 3.1 and beads 311. The magnetic distal tip 3.1 and the beads 311 with distinctly different $H_c$ values will act on each other as a mechanical joint. The two different $H_c$ values having properties that are "elastic" or "plastic" will respond to the magnetic field in a fashion of simulating an action such as cantilevered beam, and the deformation will result in an angular displacement value associated with the difference in $H_c$ between the distal tip 3.1 and beads 311. When the magnetic field is removed, the cantilevered moment of inertia will recover and return the distal tip 3.1 to the position of its natural magnetization axis.

In one embodiment a permanent magnet such as $Nd_2Fe_{14}B$ is used in forming the distal tip 3.1 of the catheter assembly 375, providing for a saturation magnetization of about 16 kG. However it is to be expressly understood that other permanent magnets now known or later devised may be used in forming the distal tip 3.1 without departing from the original spirit and scope of the invention.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for automatically mapping the interior surface of a coronary chamber comprising:
    inserting a catheter with an array of electrodes disposed on its surface into the coronary chamber;
    generating a shaped magnetic field around the catheter and coronary chamber to selectively move the catheter under closed loop control;
    receiving a plurality of signals from the electrode array disposed on the catheter;
    calculating an actual position of the catheter within the coronary chamber from the plurality of received signals;
    determining a presence of continuous or partial contact between the catheter and the surface of the coronary chamber from the plurality of received signals;
    generating an automated mapping pattern for the catheter using closed loop control for movement of the catheter to optimize the closed loop automated mapping pattern of the catheter, wherein generating the automated mapping pattern for the catheter further comprises:
        obtaining a plurality of measurements from the surface of the coronary chamber when continuous contact has been established according to the generated closed loop automated mapping pattern; and
        obtaining a plurality of measurements from the surface of the coronary chamber when partial contact has been established according to the generated closed loop automated mapping pattern;
        automatically generating a map of the continuous contact manifold of the coronary chamber based on the obtained continuous contact measurements; and
        automatically generating a map of the partial contact zone of the coronary chamber based on the obtained partial contact measurements; and
    automatically moving a distal end of the catheter between the generated map of the continuous contact manifold and the generated map of the partial contact zone during generation of the closed loop automated mapping pattern of the catheter, so that travel time and distance through the distal end of the catheter is moved during generation of the closed loop automated mapping pattern is reduced.

2. The method of claim 1 where receiving a plurality of signals from the electrode array disposed on the catheter comprises collecting a plurality of impedance measurements obtained from the coronary chamber and where determining the presence of continuous or partial contact between the catheter and the surface of the coronary chamber comprises determining the presence of continuous or partial contact based on the impedance measurements obtained by the electrode array.

3. The method of claim 1 where obtaining a plurality of measurements from the surface of the coronary chamber when continuous contact has been established according to the generated closed loop automated mapping pattern further comprises:
    guiding the catheter towards the surface of the coronary chamber until continuous contact between the coronary chamber and the catheter is determined; and
    maintaining surface contact between the coronary chamber and the distal tip of the catheter over several systole/diastole cycles; and
    where obtaining a plurality of measurements from the surface of the coronary chamber when partial contact has been established according to the generated closed loop automated mapping pattern comprises retracting the catheter from the surface of the coronary chamber until partial contact between the coronary chamber and the catheter is determined.

4. The method of claim 3 wherein the steps of guiding the catheter towards the coronary chamber surface and retracting the catheter away from the coronary chamber surface comprises automatically altering the shape of the generated magnetic field and automatically adjusting a field strength of the generated magnetic field.

5. The method of claim 3 where retracting the catheter away from the coronary chamber surface comprises retracting the catheter to the partial contact zone defined a distance away from the surface of the coronary chamber.

6. The method of claim 3 further comprising repeating the steps of guiding and maintaining the catheter for a plurality of different desired contact points along the surface of the coronary chamber.

7. The method of claim 1 where generating an automated mapping pattern for the catheter using closed loop control for movement of the catheter to optimize the closed loop automated mapping pattern of the catheter comprises:
    guiding the catheter from its actual position to the first of a series of desired positions along the surface of the coronary chamber;
    obtaining a plurality of measurements from the first of a series of desired positions when continuous contact has been achieved;
    retracting the catheter from the first of a series of desired positions; and
    automatically guiding the catheter to the next desired position within the series until measurements have been obtained from every desired position within the automated mapping pattern.

8. The method of claim 7 further comprising differentiating between at least two different types of tissue within the coronary chamber based on the measurements obtained at each of the desired positions.

9. The method of claim 8 further comprising adding results of the tissue differentiation to the generated map of the coronary chamber.

10. An apparatus for automatically mapping the interior surface of a coronary chamber comprising:
    a catheter capable of entering the coronary chamber;

means for generating a shaped magnetic field around the catheter and coronary chamber to selectively move the catheter using closed loop control;

means for determining a presence of continuous or partial contact between the catheter and the surface of the coronary chamber;

means for generating a closed loop automated mapping pattern for the catheter based on continuous or partial contact between the catheter and the surface to the coronary chamber;

means for optimizing the closed loop automated mapping pattern of the catheter wherein the means for optimizing further comprise:

means for obtaining a plurality of measurements from the surface of the coronary chamber when continuous contact has been established according to the generated closed loop automated mapping pattern;

means for obtaining a plurality of measurements from the surface of the coronary chamber when partial contact has been established according to the generated closed loop automated mapping pattern;

means for automatically generating a map of the continuous contact manifold of the coronary chamber based on the obtained continuous contact measurements; and means for automatically generating a map of the partial contact zone of the coronary chamber based on the obtained partial contact measurements;

means for automatically moving a distal end of the catheter between the generated map of the continuous contact manifold and the generated map of the partial contact zone during generation of the closed loop automated mapping pattern of the catheter, so that travel time and distance through the distal end of the catheter is moved during generation of the closed loop automated mapping pattern is reduced; and a display for displaying a map of the coronary chamber generated by the obtained continuous contact measurements.

11. The apparatus of claim 10 where the means for generating a shaped magnetic field around the catheter and coronary chamber comprises a plurality of electromagnetic coils disposed substantially symmetrically about the coronary chamber and catheter.

12. The apparatus of claim 10 where the means for determining the presence of continuous or intermittent contact between the catheter and the surface of the coronary chamber comprises a plurality of impedance sensing electrodes disposed on the surface of the catheter.

13. The apparatus of claim 10 where the means for optimizing the closed loop automated mapping pattern of the catheter comprises means for the catheter to be guided to and retracted from the surface of the coronary chamber via the shaped magnetic field.

14. The apparatus of claim 10 where the means for obtaining a plurality of measurements from the surface of the coronary chamber when continuous contact has been established comprises means for differentiating between at least two different types of tissue within the coronary chamber.

15. The method of claim 14 further comprising means for adding results of the tissue differentiation to the display of the map of the coronary chamber.

16. The apparatus of claim 10 further comprising means for preventing the catheter from exceeding the partial contact zone defined a distance from the surface of the coronary chamber.

* * * * *